US011950851B1

(12) United States Patent
Roh et al.

(10) Patent No.: US 11,950,851 B1
(45) Date of Patent: Apr. 9, 2024

(54) DIGITAL IMAGE ANALYSIS FOR DEVICE NAVIGATION IN TISSUE

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US); Adam Benson, Missoula, MT (US); Julie Benson, Missoula, MT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/968,177

(22) Filed: Oct. 18, 2022

(51) Int. Cl.
*A61B 34/10* (2016.01)
*A61B 34/20* (2016.01)

(52) U.S. Cl.
CPC .............. *A61B 34/10* (2016.02); *A61B 34/20* (2016.02); *A61B 2034/105* (2016.02); *A61B 2034/107* (2016.02); *A61B 2034/2065* (2016.02)

(58) Field of Classification Search
CPC .......... G06N 20/00; G06N 3/045; G06N 3/02; A61B 34/30; A61B 34/25; A61B 34/20; A61B 90/361; A61B 34/10; A61B 90/37; A61B 2034/107; A61B 2034/2065; A61B 2034/105; A61B 2034/104; A61B 2034/101; A61B 5/0077; A61B 1/00154; A61B 1/00194; A61B 34/70; A61B 5/00; A61B 5/004; A61B 2576/00; A61B 5/0013; A61B 5/0036; A61B 5/4836; G06V 2201/03; G06V 2201/034; G16H 30/40; G16H 40/40; G16H 40/60
See application file for complete search history.

(56) References Cited

U.S. PATENT DOCUMENTS 9,600,138 B2 * 3/2017 Thomas ................... G06T 19/20
2021/0212782 A1 * 7/2021 Shelton, IV ........... G16H 40/40

* cited by examiner

*Primary Examiner* — Deborah L Malamud
(74) *Attorney, Agent, or Firm* — Perkins Coie LLP

(57) ABSTRACT

Methods, apparatuses, and systems for digital image analysis for device navigation in tissue are disclosed. The disclosed system uses real-time angiography and artificial intelligence to navigate an end effector of a surgical robot through a patient's vasculature to provide a surgical intervention. Digital imaging is performed that enables three-dimensional mapping of the patient's vasculature. Locations and movement of the end effector of the surgical robot are determined. The end effector is used to perform an intervention such as the removal of a blood clot or delivery of a drug for dissolving a blood clot.

17 Claims, 13 Drawing Sheets

PATIENT DATABASE

| Patient ID | Age | Gender | Height (in.) | Allergies | Conditions | Image Files |
|---|---|---|---|---|---|---|
| M_0026 | 46 | Male | 70 | None | None | MRI_pelvis_3-20-2022 |
| F_0165 | 36 | Female | 65 | None | None | XRAY_r-knee_2-4-2022 |
| F_0654 | 48 | Female | 68 | Latex | Breast Cancer | CT_chest_1-5-2022 |
| M_0264 | 65 | Male | 72 | None | Coronary Heart Disease | CT_chest_2-16-2022 |
| F_0544 | 72 | Female | 63 | None | Osteoporosis | XRAY_pelvis_2-25-2022 |

*FIG. 8*

| Procedure ID | Patient ID | Surgeon ID | Procedure |
|---|---|---|---|
| 465463 | M_0026 | 1654 | Thrombectomy |
| 847324 | F_0165 | 1548 | Stent Placement |
| 321698 | F_0654 | 1265 | Medication Delivery |
| 765864 | M_0264 | 1874 | Angioplasty |
| 679465 | F_0544 | 1324 | Thrombectomy |

*FIG. 9*

DIGITAL IMAGE ANALYSIS FOR DEVICE NAVIGATION IN TISSUE

TECHNICAL FIELD

The present disclosure is generally related to automated and robotic surgical procedures and specifically to apparatuses for performing robotic surgical procedures using automated disease detection by multiple-wavelength imaging.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 8 is a chart illustrating a patient database, in accordance with one or more embodiments.

FIG. 9 is a chart illustrating a procedure database, in accordance with one or more embodiments.

DETAILED DESCRIPTION

Figure 1:
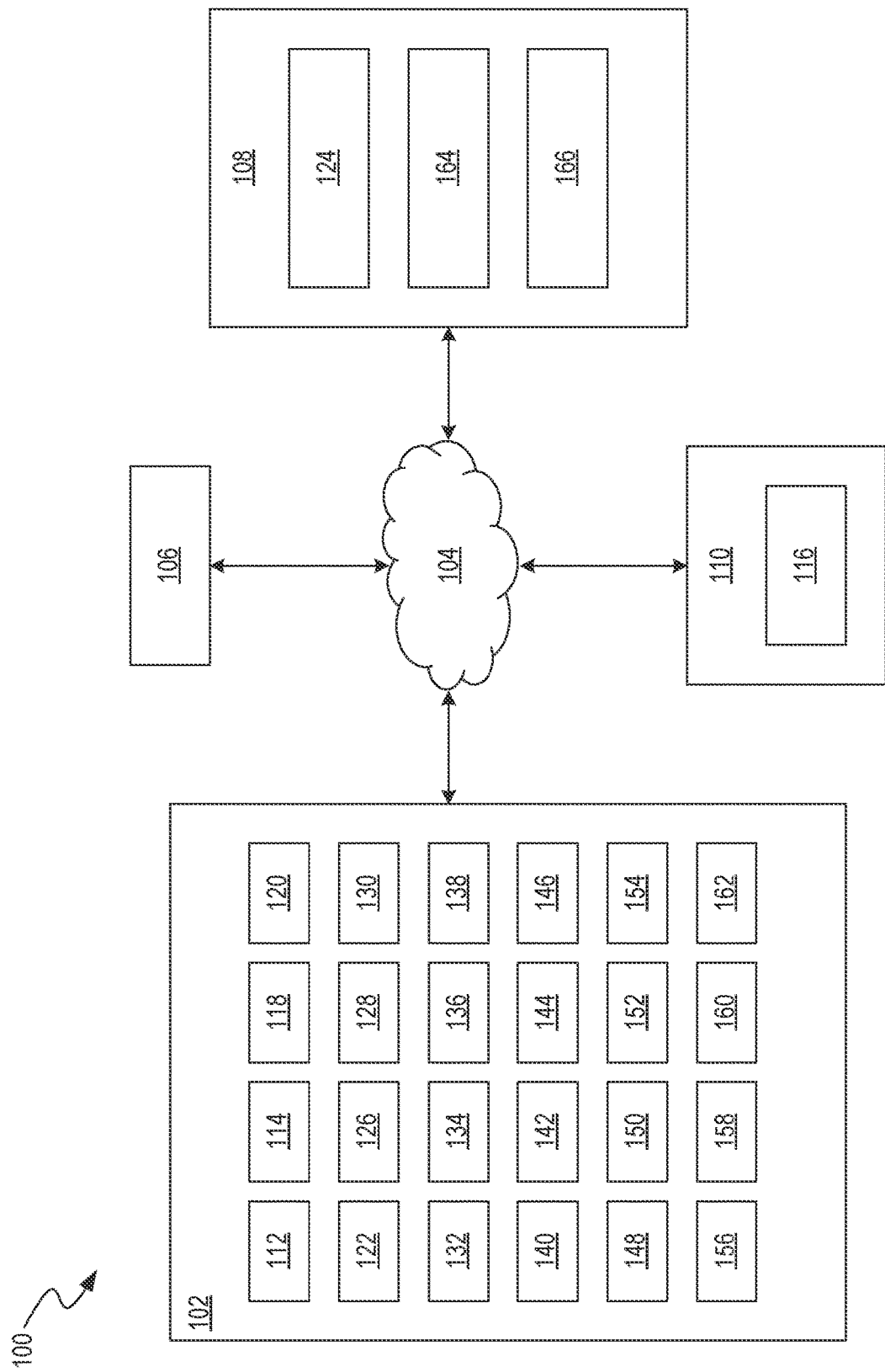
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610a") described as a single instance. Further, plural instances (e.g., "610") refer collectively to a set of components, operations, or structures (e.g., "610a") described as a single instance. The description of a single component (e.g., "610a") applies equally to a like-numbered component (e.g., "610b") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

In embodiments, medical imaging is performed using different wavelengths of electromagnetic energy, ultrasounds, magnetic resonance, etc. The different wavelengths when directed towards a subject, such as bone tissue, soft tissue, or any other subject or substance, image different types of tissues with varying depths of penetration. For example, when visible light of a predefined wavelength is directed at bone tissue, a part of the incident light can be absorbed by the bone tissue. As a result, the intensity of the reflected/refracted light is less than that of the incident light. The decrease in the intensity of the incident light can be measured and used to generate an image. In embodiments, different medical devices having capabilities including, but not limited to, X-ray imaging, magnetic resonance imaging (MRI), ultrasound, angiography (e.g., an examination by X-ray of blood or lymph vessels, executed after introduction of a radiopaque substance), or computer tomography (CT) are used. In embodiments, omni-tomographic imaging or grand fusion imaging, such as large-scale fusion of simultaneous data acquisition from multiple imaging modalities (e.g., CT, MRI, PET, SPECT, USG, or optical imaging), is used. Composite images, including image data from multiple modalities, are sometimes referred to as "multi-modality images" or "multiple-modality images" herein.

Traditional radiologic images often requires specialized training for radiologists to acquire and interpret the images. However, with the increasing use of radiologic imaging, a radiologist may not necessarily be present to assist with a surgical procedure. While advancements in imaging technologies have made acquiring radiologic images easier, surgeons and other treatment specialists must still interpret the images but with far more limited training than radiologists. Angiography can be used to diagnose conditions involving vasculature of the circulatory and lymphatic systems. For example, a dye can be used to help blood fluoresce under X-Rays to improve visibility of the vessels. However, identifying and diagnosing conditions such as thrombosis, hemorrhage, or other conditions, which are not obvious to the untrained eye pose challenges. For example, absence of blood flow can indicate a thrombosis as the blood cannot pass by the clot. However, identifying a location of the clot can be challenging. Similarly, studying a hemorrhage requires careful analysis to identify the location of the bleeding vessel. When such conditions result in stroke or heart attack, rapid identification and intervention is critical.

The embodiments disclosed herein describe methods, apparatuses, and systems for digital image analysis for device navigation in tissue. In some embodiments, multiple imaging modalities are used for assessing a medical condition. Data collected from multiple cameras and imaging modalities are processed to identify common structures. The common structures are used to scale and align images, which are analyzed to detect one or more medical conditions. Each acquired image is assessed, and the resulting probabilities are consolidated. The images can be assessed together by using artificial intelligence and machine learning. In embodiments, real-time angiography and artificial intelligence are used to guide an end effector of a surgical robot through a patient's vasculature to provide a surgical intervention. Digital imaging is performed that enables three-dimensional mapping of the patient's vasculature. Locations and movement of the end effector of the surgical robot are determined. The end effector is used to perform an intervention such as the removal of a blood clot or delivery of a drug for dissolving a blood clot.

In some embodiments, systems, methods, and techniques are provided for navigating a surgical instrument through a vasculature of a patient using a surgical robot. For example, the systems may obtain one or more images of an anatomy of the patient using one or more imaging devices and identify one or more anatomical structures of the anatomy by performing digital image analysis on the one or more images. The system may generate a mapping of the vasculature in a plurality of dimensions based on the one or more anatomical structures and determine, by a machine learning model using the mapping, an anomalous condition within the vasculature. The system can determine an incision site on the anatomy for inserting the surgical instrument into the anatomy based on the mapping and the anomalous condition, determine a treatment site based on a location of the anomalous condition, and generate a route for navigating the surgical instrument from the incision site to the treatment site through the vasculature, the route comprising at least a portion of one or more blood vessels. The system may also insert, by the surgical robot, the surgical instrument into the anatomy at the incision site and navigate, by the surgical robot, the surgical instrument from the incision site to the treatment site along the route to treat the anomalous condition.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The imaging systems disclosed use computer networks, the Internet, intranets, and supporting technologies to implement a cost-effective technology to collect, transmit, store, analyze, and use imaging information in electronic formats. As a result, surgical robots can use the embodiments to collect and analyze vast amounts of information, resulting in early diagnoses. The disclosed methods reduce the amount of noise and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to a surgical robot or surgeon during a surgical procedure.

The disclosed embodiments address complex vasculature that can otherwise be difficult to navigate using conventional systems. For example, the disclosed apparatus provides efficient and effective methods to navigate blood vessels that branch, where taking a less optimal route can require backing out of a branch and having to try another route. The disclosed methods that enable the identification of a path from an incision site to a treatment site and guidance of a catheter along the path provide the ability to rapidly diagnose a blood clot, hemorrhage, or other potentially life-threatening condition in a patient's vasculature successful treatment of strokes and heart attacks. Moreover, the automated systems disclosed alleviate the requirements of having a skilled radiologist available to make diagnoses. Further, the apparatus can quickly identify a beneficial path to a clot and guide a catheter while avoiding less-optimal branches to reduce surgical time and likelihood of injury, and improve the chance of positive patient outcomes.

The embodiments provide automated and more efficient systems for using multiple imaging modalities, especially those using different wavelengths of electromagnetic waves. Quicker diagnosis of patients is achieved compared to traditional methods via simultaneous or sequential imaging. The automated methods of aligning images taken using different imaging modalities disclosed provided improved analysis of the images to identify medical conditions. In addition, the advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

Advantageously, the image analysis can be performed from a single imaging reference position or range of known positions (e.g., multiple locations having known relative positions to create a well-posed relationship) to enable position-independent correlating of values, images, and/or captured data. In embodiments, multiple-imaging devices are implemented. A multiple-imaging device can capture different images using different imaging modalities. In single imaging reference position embodiments, output from a multiple-imaging device can be directly combined to provide composite multi-modality analysis. For example, the system can select and process (e.g., using different weights, filters, etc.) output from one or more of the multiple-imaging devices. The processed output can then be combined with output (e.g., image data, images, video, etc.) from any other devices (e.g., imaging devices, CT scanners, cameras, X-ray machines, and the like). The relative positions between the imaging devices can be stored by the system. The system can then process the data (e.g., transform the data, modify or scale the data, etc.) to provide for enhanced interpretation by a physician. Transformation matrices can be stored to combine outputs from imaging devices located at different positions during tissue analysis. Advantageously, the transformation matrices allow for accurate analysis of the same tissues, features, or the like when using multiple-imaging devices. Further, the resulting composite analysis can then be overlaid onto image data to generate two-dimensional (2D) or three-dimensional (3D) multi-modality renderings, topological maps, pictures, video, or other image data to produce a diagnostic image or map, which can be annotated by a user or a system programmed for annotation, etc., to facilitate user review. The transformation matrices can be selected based on the modalities used to capture the images.

The resulting outputs can be selected and correlated to generate one or more diagnoses based on, for example, patient information (e.g., age, condition, status, etc.), accuracy scores for the individual values, machine-learning models, and/or various combinations thereof. The methods disclosed herein can correlate images (e.g., composite images, multi-modality images, single-modality images, etc.) to reference cases to identify similar individuals with known conditions. Then the reference cases (and the combined measurements) are used to diagnose an individual's condition. Accordingly, the systems and methods disclosed herein provide an accurate assessment of the individual's condition.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph (e.g., an instrument for recording and measuring variation in the volume of a part of the body, especially as caused by changes in blood pressure) or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal $CO_2$ monitor or capnography monitor used for measurement of the level of carbon dioxide that is released at the end of an exhaled breath (referred to as end-tidal carbon dioxide, $ETCO_2$). Capnography may refer to the noninvasive measurement of the partial pressure of carbon dioxide ($CO_2$) in exhaled breath expressed as the $CO_2$ concentration over time. An end-tidal $CO_2$ monitor or capnography monitor is widely used in anesthesia and intensive care. $ETCO_2$ can be calculated by plotting expiratory $CO_2$ with time. Further, $ETCO_2$ monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal $CO_2$ monitor can be configured as side stream (diverting) or mainstream (non-diverting). A diverting end-tidal $CO_2$ monitor transports a portion of a patient's respired gases from the sampling site to the end-tidal $CO_2$ monitor, while a non-diverting end-tidal $CO_2$ monitor does not transport gas away. Also, measurement by the end-tidal $CO_2$ monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory (e.g., based on the detection of Korotkoff sounds issued from the acoustic transducer signal) or oscillometric (e.g., using air volume variations detected during deflation of a cuff).

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals (e.g., relating to electrical impulses such as those generated by muscles of the body) such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis (e.g., the stopping of a flow of blood) and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. A laparoscope as referenced herein may mean a fiber-optic instrument inserted (e.g., through an abdominal wall) for viewing organs in the abdomen or to permit surgery on a small scale. The laser 132 is used in MIS to ablate soft tissues, such as a herniated spinal disc bulge. A surgical tool may also be referred to as a surgical instrument herein.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty (e.g., a procedure for repairing a heart valve that has a narrowed opening).

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. Stereotactic, as referenced herein, may mean relating to techniques for surgical treatment or investigation permitting accurate positioning of probes within the body, based on three-dimensional diagrams. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the 02 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy (e.g., a surgical procedure that involves cutting bone or adding bone tissue to reshape or realign bones) of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures (e.g., previous procedures of the patient and/or of other patients). The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In embodiments, the system 100 uses quantum computing. Quantum computing refers to the use of a computational device or method that uses properties of quantum states defined by quantum mechanics such as superposition, entanglement, etc., to perform computations. Quantum devices use qubits, which are the quantum equivalent of bits in a classical computing system. Qubits have at least two quantum states or probable outcomes. These outcomes, combined with a coefficient representing the probability of each outcome, describes the possible states, or bits of data, which can be represented by the qubits according to the principle of quantum superposition. These states can be manipulated to shift the probability of each outcome, or additionally, add additional possible outcomes to perform computations, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows the greatest promise for drug discovery and simulating the interaction of drugs with biologic systems, however the same technology can also be used to predict the interaction of a biologic system with an implanted device, preventing rejection of an implant by a patient's body. Quantum computing can be used to investigate long term functioning of an implant. Further, quantum computing can be used to study the reaction of a patient to a surgical procedure, during a simulation, before a procedure, or actively during a procedure.

Figure 2:
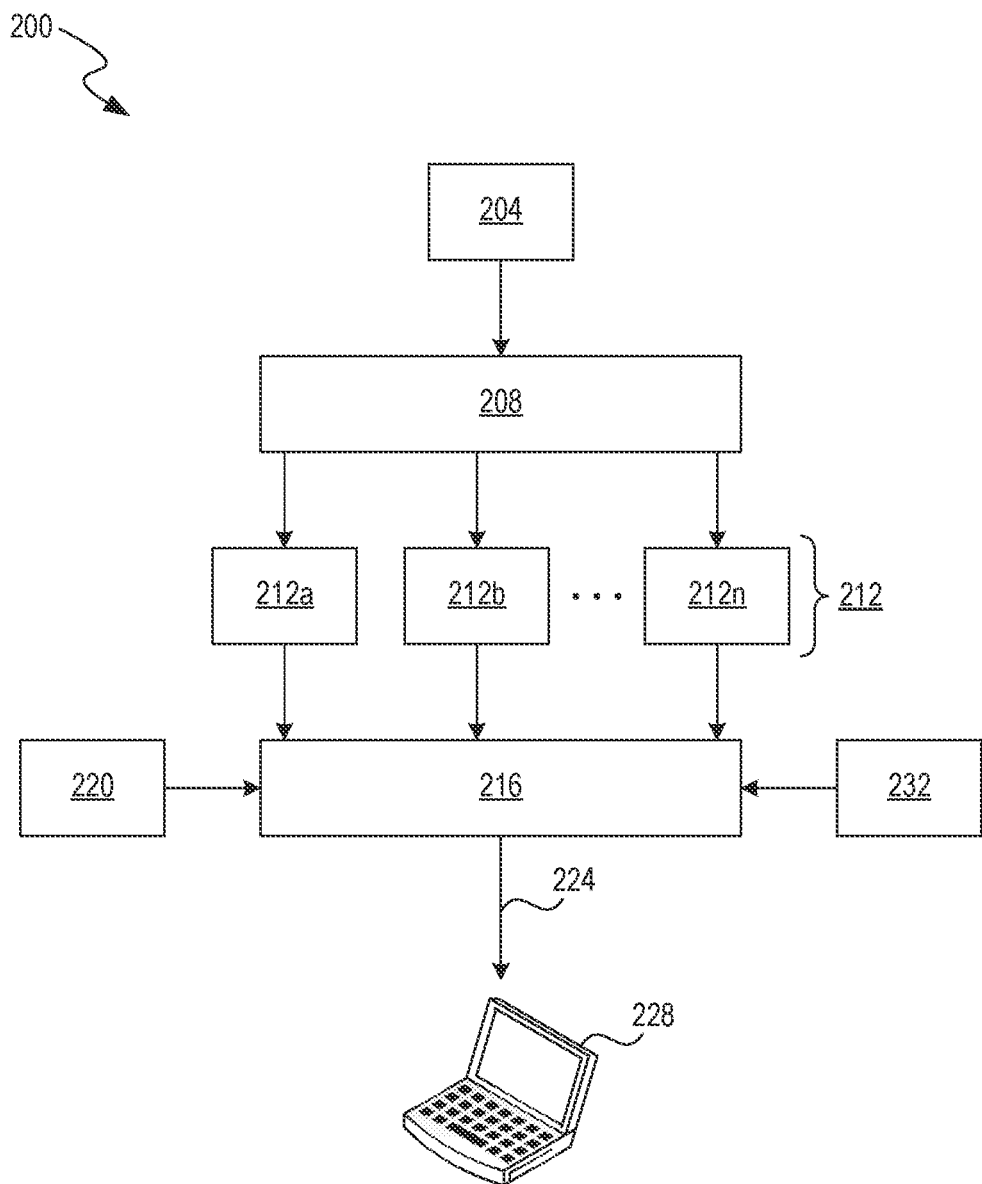
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
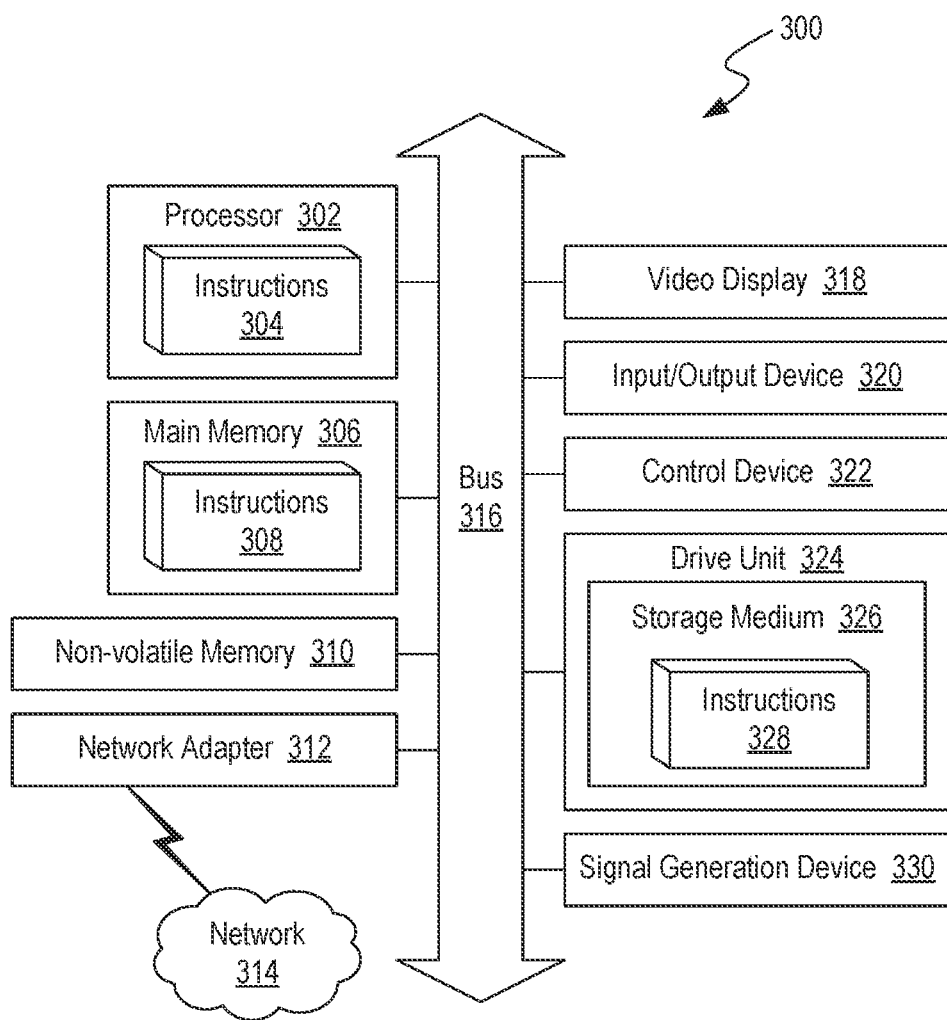
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
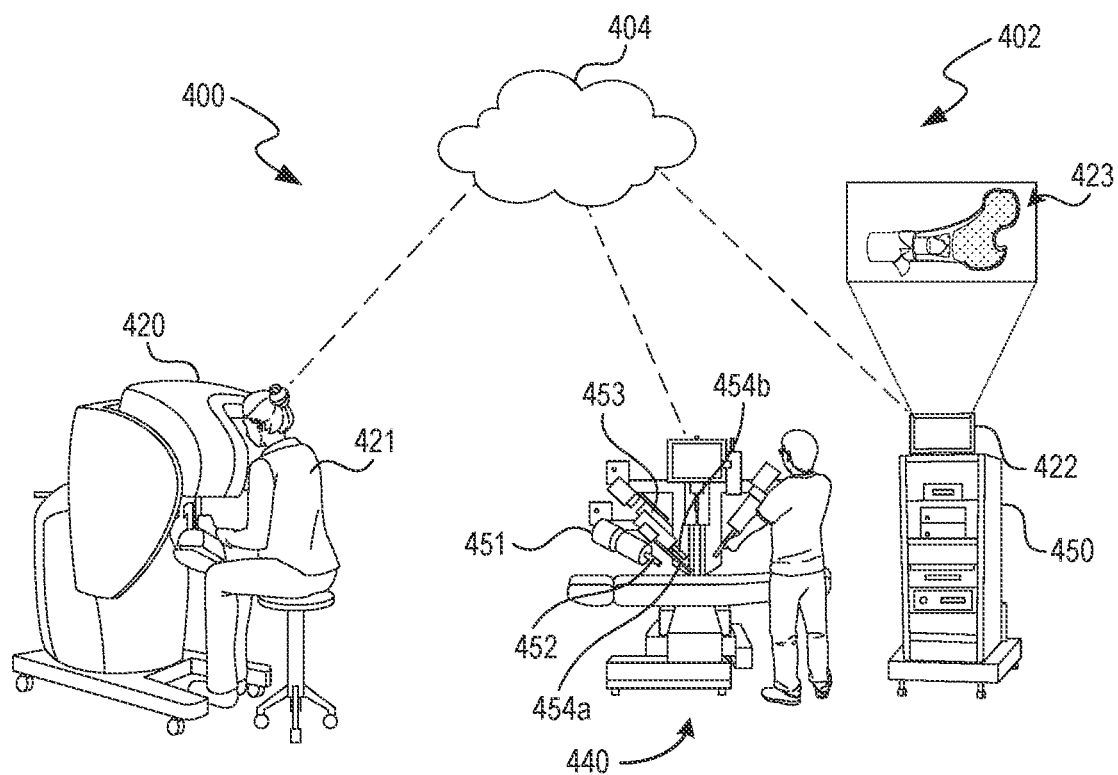
FIG. 4A is a block diagram illustrating an example robotic surgical system, in accordance with one or more embodiments.

FIG. 4A is a block diagram illustrating an example robotic surgical suite or system 400 ("robotic surgical system 400"), in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1). The robotic surgical system 400 can be configured to provide telepresence control by one or more consultants at remote locations based on a pre-operative surgical plan, inter-operative surgical event(s) at the surgical suite, etc. Machine learning algorithms and other techniques disclosed herein can be used to manage surgical suite resources, schedule consultants, manage permission rights, and/or adjust network flow to improve surgical outcomes. For example, flow of network traffic at the surgical suite can be controlled to maintain a threshold level of control of the medical equipment by the user.

The robotic surgical system 400 includes a user device or console 420 ("console 420"), a surgical robot 440, and a computer, controller, or data system 450. The console 420 can be on-site or at a remote location and operated by a surgeon and can communicate with components in a surgical suite or an operating room 402 ("operating room 402"), remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc., or other features disclosed herein to perform surgical step(s) or procedures or implement steps of processes discussed herein.

A consultant device can communicate via the network 404 with components of the robotic surgical system 400, monitoring equipment, or other components of the robotic surgical system 400. The surgical robot 440, or other components disclosed herein, can communicate with and send collected data (e.g., sensor readings, instrument data, surgical robot data, etc.) to at least one database or data system 450, which are accessible to the consultant(s). This information can be used to, for example, create new machine-learning training data sets, generate procedure plans, perform future simulations, post-operatively analyze surgical procedures, or the like. The controller or data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A mobile network test module may measure the latency of the wireless communication established between the robotic surgical system and the consultant device to manage network flow. A measured/determined latency of a wireless network may be the same as a latency of a network that includes the wireless network, where the network may include a starting point/node for data to be transmitted to an ending point/node, and where the data is communicated by one computer/device associated with a surgical site to another computer/device associated with a location of the remote physician/surgeon. Scheduling of consultants can be based, at least in part, on expected latency (e.g., latency within the network 404 or other network) required to perform the telesurgery based on the received one or more surgery data. For example, a scheduling module may be configured to determine the requirement of the bandwidth (e.g., 10 MHz, 20 MHz, 30 MHz, etc.) needed and/or expected latency (e.g., ±50 milliseconds, ±70 milliseconds, ±100 milliseconds, etc.). The parameters for scheduling participation of the consultant device can be selected by a surgical team, healthcare provider, or the like.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
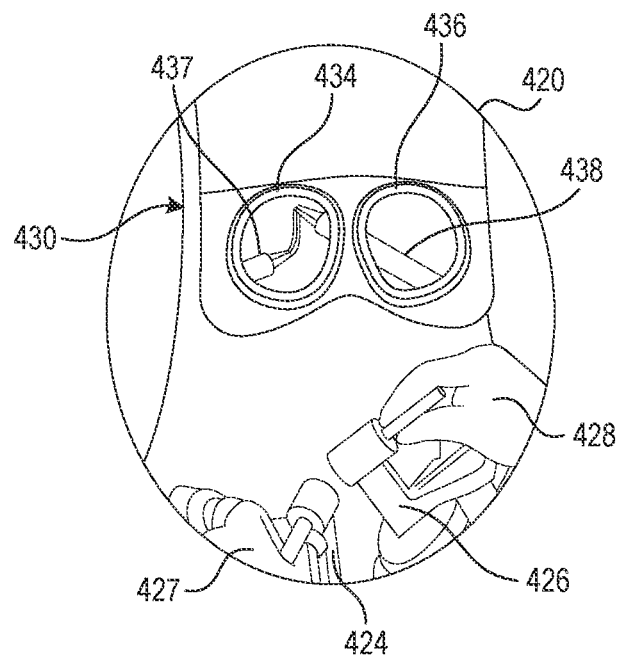
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, image modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454a, 454b (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from standalone X-ray machines, MRI machines, CT scanners, etc. Example imaging devices and imaging modalities are discussed in connection with FIGS. 1, 4A, and 6. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, a machine learning system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the machine learning system. Newly-captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic (s), margins, etc.), features of interest, anatomical elements (e.g., cartilage, soft tissue, etc.), or the like. An example image is discussed in connection with FIG. 5. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

Referring to FIG. 4A, a consultant device can display procedure information from the surgery room, equipment controls, and other data disclosed herein. The consultant device can display a graphical user interface ("GUI") for telepresence consulting. The GUI includes an authorization input for authorizing the consultant for participation in a surgical procedure and displays procedure and patient data. Imaging equipment can automatically capture images for surgical side viewing via a display. The GUI includes a procedure progress that can be updated to show completed progress for the procedure, and controls can be used to operate machines/applications. The user can customize the GUI by rearranging the displayed items for convenience.

The consultant can use an authorization input to, for example, input user authorization information (e.g., access codes, pins, etc.), employee credential information, surgical procedure information (e.g., serial number or code for the surgical procedure), or the like to access and operate equipment. If the consultant needs additional permission rights, the consultant can request the additional permission rights using the authorization input. For example, if an adverse event occurs during the procedure requiring the consultant to provide additional care, the consultant can request access to the additional equipment (e.g., robotic arms of surgical robot, breathing machine, heart rate monitor, etc.) via the authorization input. The surgical suite system can receive the requested authorization and perform an authorization protocol routine to determine whether the consultant should be granted permission rights to the additionally requested equipment. The surgical suite system can analyze the surgical plan, planned permission rights (e.g., plan of permission rights assigning permission rights to features or steps of the surgical plan), consultant credentials and/or expertise, and/or other information disclosed herein to determine whether to grant permissions. If requested permission rights are denied, the on-site medical team can be notified of the denied request and consultant input, recommendation, etc. If the request is granted, the system can automatically establish communication and control channels for displaying the additional information for the additional equipment via the consultant device. The procedure progress can show completed progress for the modified procedure based on the additional equipment.

Dynamic updating of the equipment controls on the consultant device allows the user to acquire control of additional medical equipment in the same consulting session without disrupting communication channels. This reduces the risk of latency and/or network problems that could affect the medical procedure. The controls can be configured to perform all or some of the controls as discussed in connection with FIG. 4B. For example, the controls can include a touch input control module with input features that can be used to increase or decrease, respectively, settings of equipment. The touch input control module can be used to control movement of, for example, robotic surgical arms, robotic manipulators, and effectors, or the like. For example, the touch input control module can be configured to provide the same controllability as the hand-operated input devices 424, 426 of FIG. 4B. In some embodiments, the controls can be modified to include controls for the additional equipment such that the consultant has access to controls for operating newly available equipment in real-time while continuing to view real-time patient data. Data collected by and/or associated with additional equipment can automatically be added to the patient data.

The consultant device can include a procedure viewer, a surgical suite or room viewer, and/or other viewers or windows for providing viewing (e.g., real-time or near real-time viewing) of the surgical suite (e.g., viewing at operating rooms, recovery rooms, etc.), medical team, medical equipment, etc. The consultant device can display patient data that can include, for example, blood pressure, health rating, heart rate, body temperature, vitals, physician notes, and/or additional patient data useful to the consultant. To change or receive additional patient data, the consultant can use a request data button to send a message or notification to the on-site surgical team to provide additional patient data. The consultant can use a talk feature to verbally communicate with the surgical team. The consultant device can also display the surgical team information. The surgical team information can list physicians, nurses, staff, consultants, and other staffing information.

The robotic surgical system 400, illustrated and described in more detail with reference to FIG. 4A, can further include multiple consultant devices so that multiple members of a surgical team or consultants can view the surgical procedure. The number and configuration of the consultant devices can be selected based on the configuration and number of surgical robots, monitoring equipment, etc. The consultant device can also display procedure data, including a surgical plan (e.g., a surgical plan including completed and future planned surgical steps), patient monitor readings, surgical suite or room information (e.g., available team members, available surgical equipment, surgical robot status, or the like), images (e.g., pre-operative images, images from simulations, real-time images, instructional images, etc.), and other surgical assist information. In some embodiments, the consultant device can be an AR/VR headset, display, or the like.

Referring to FIG. 4A, the robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through artificial intelligence mapping. The software for artificial intelligence is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
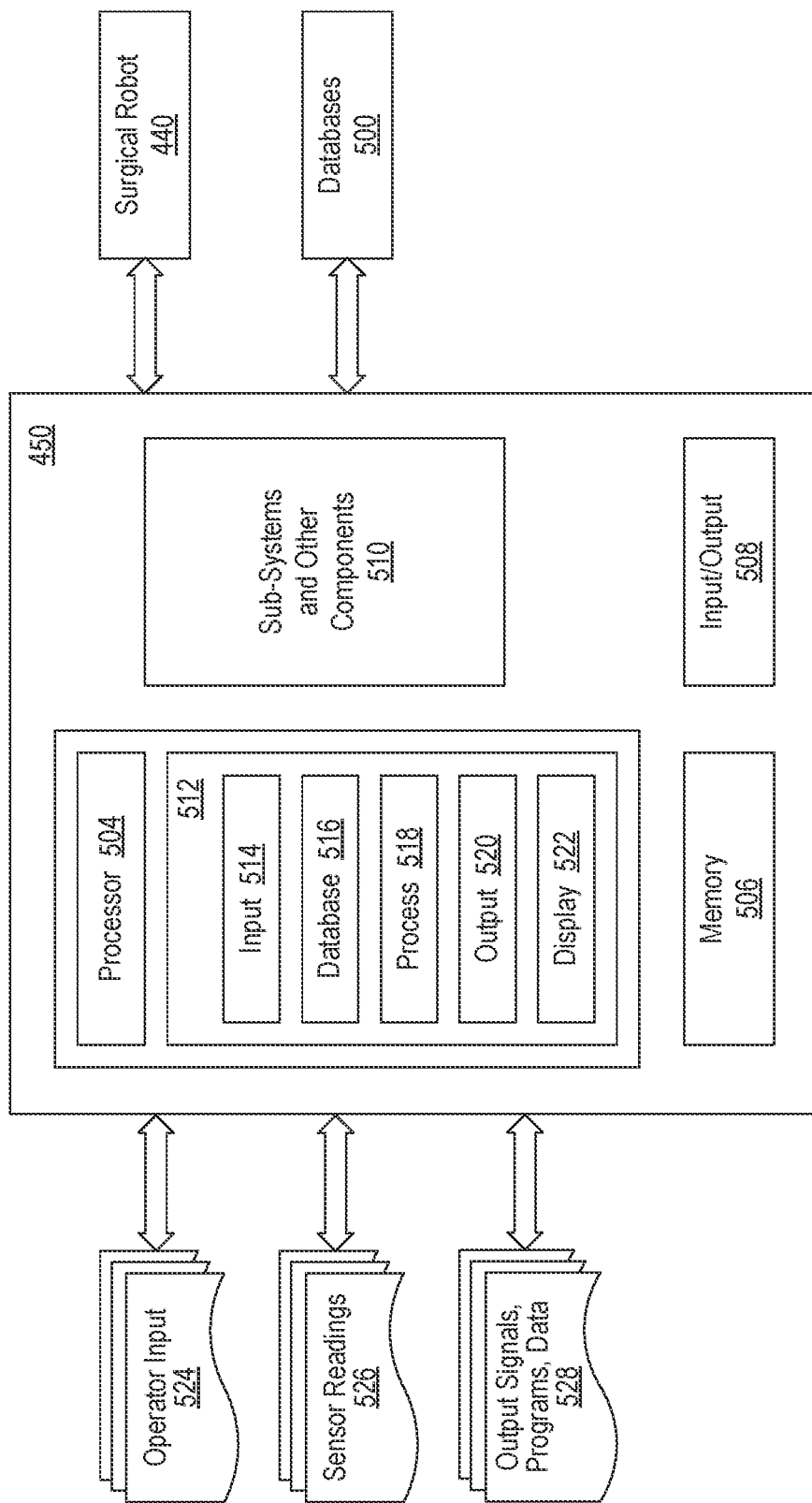
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The controller or data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices (including consultant devices), and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-program mable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A network adapter 501 can be an operator authorizing device to manage communications and operation of components, as described with reference to FIG. 3. The network adapter 501 can govern and/or manage permissions to access proxy data in a computer network, track varying levels of trust between different machines and/or applications, and manage control access to surgical equipment, communications between remote devices and the surgical room, etc.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6:
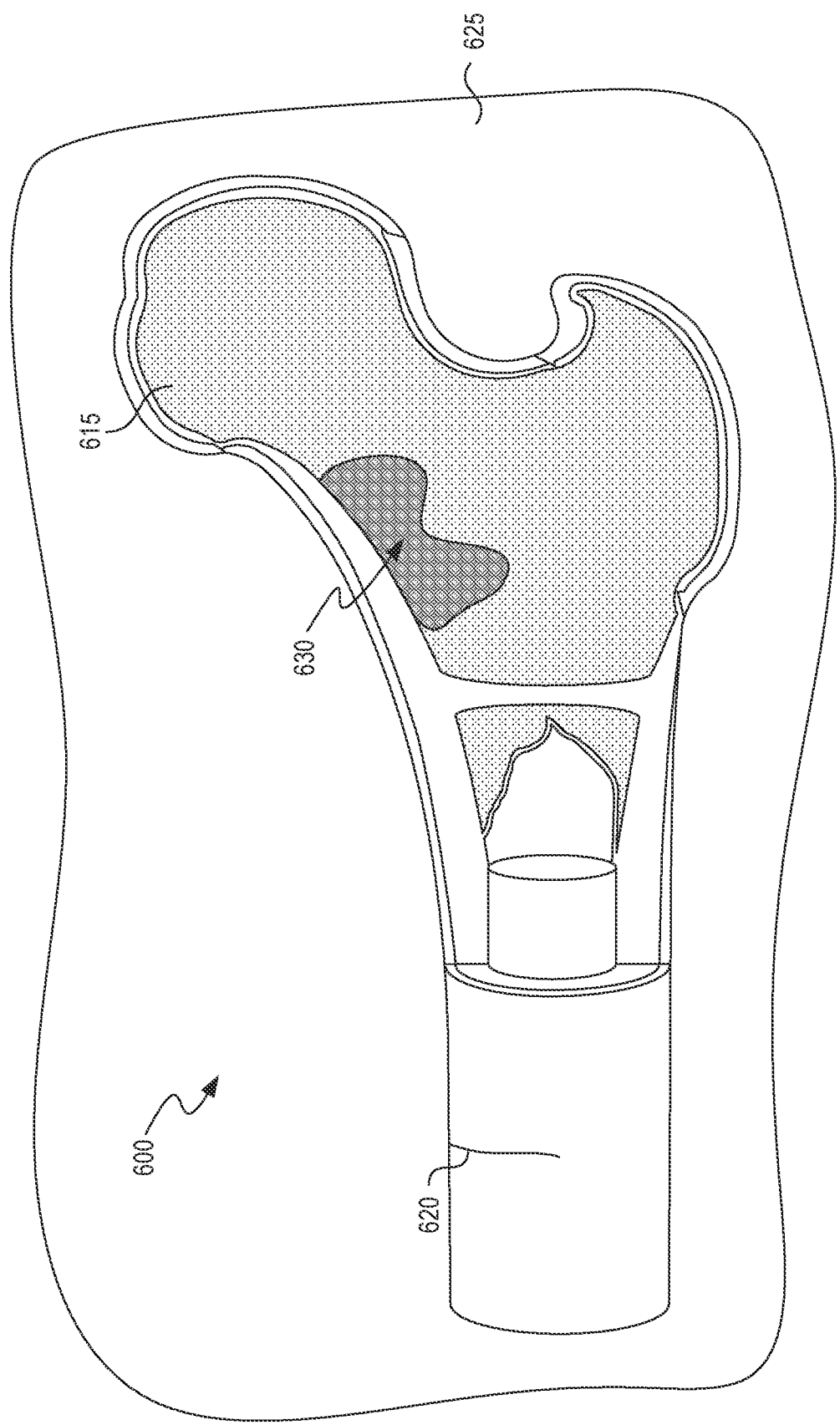
FIG. 6 illustrates an example multi-modality image of a target region, in accordance with one or more embodiments.

FIG. 6 illustrates an example of an image 600, in accordance with one or more embodiments. The image 600 can allow a healthcare worker to view a target region 625 to analyze an automated diagnosis, anatomical features, identify tissue of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 600 (e.g., a pre-operative image, real-time intra-operative image, etc.). The multi-modality image 600 can be generated based on a surgical plan, physician input, or other input data, and can indicate features (e.g., anatomical elements), margins, tissue type, etc.

To generate the image 600, systems disclosed herein can receive a tissue density image from an MRI device, a bone fracture image from a CT scanner, a bone degeneration or cancerous tissue image from an ultrasound machine, or images from other imagers disclosed herein. In embodiments, the image 600 is generated for a surgical plan for treating a damaged bone and can include, for example, tissue density data 615 (e.g., healthy tissue data from an MRI device), a bone fracture 620 (e.g., identified using a CT scan), diseased tissue 630 (e.g., low-density tissue, cancerous tissue, etc., from ultrasound images), or the like. The system can combine the data to generate the image 600 with features and/or information of interest. In some embodiments, the image 600 highlights regions 625 of a tissue sample according to the diagnoses and/or the values from a multi-modality device or multiple imaging devices. For example, the image 600 can annotate highlight and/or otherwise identify/emphasize features of interest. The emphasis can help direct the doctor's review of the target region 625 and/or further analysis of the patient. In embodiments, images are generated that include raw data and multi-modality images (e.g., composite images, a multi-layer overlaid image, etc.) to allow a physician to perform an independent diagnosis. In embodiments, the raw data is indicated via differences in shading, color, fill patterns, express indications, display tables, selectable displays, and/or in any other suitable manner.

The multi-modality images can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer, surgical plan (e.g., features of interest, anatomical elements, etc.). For example, the image 600 of FIG. 6 can include selectable layers each with one or more anatomical features identified (e.g., via annotation, false colors, etc.).

Figure 7:
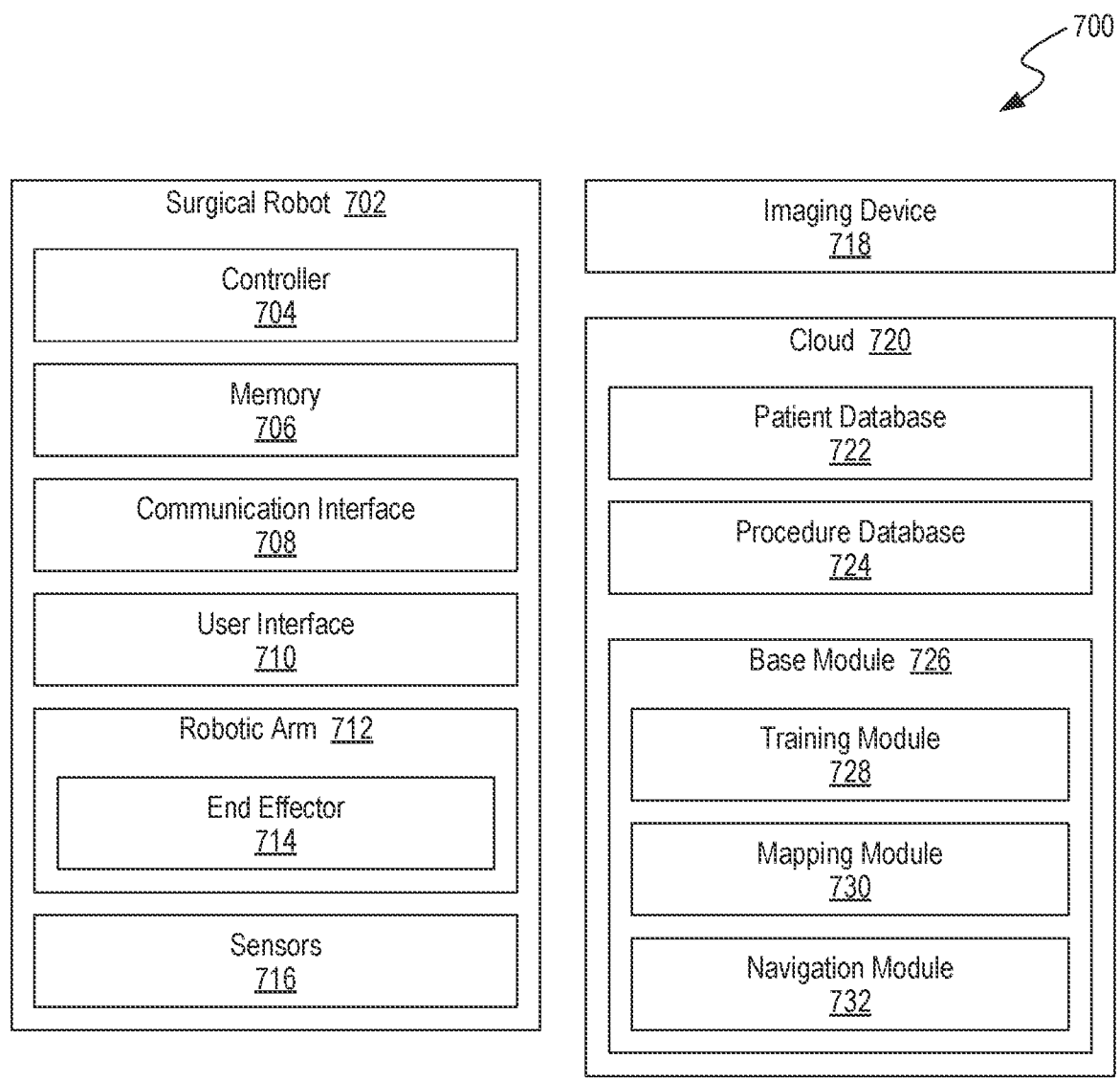
FIG. 7 is a block diagram illustrating an example robotic surgical system, in accordance with one or more embodiments.

FIG. 7 is a block diagram illustrating an example robotic surgical system 700, in accordance with one or more embodiments. The system 700 includes a surgical robot 702, which is a robotic system designed to assist a surgeon in performing a surgical operation on a patient. The system 700 can be incorporated into or used with technology discussed in connection with FIGS. 1-6. For example, one or more components of the system 700 can be incorporated into the operating room 102 discussed in connection with FIG. 1. A user interface and/or imaging device of the system 700 can be part of the console 420 discussed in connection with FIG. 4B. Output from the system 700 can be transmitted to the data system 450 in FIG. 4A and/or various other components disclosed herein. Accordingly, the system 700 can be incorporated into robotic surgery systems, or utilized to perform manual surgical procedures or to perform other procedures disclosed herein. Portions of the system 700 are implemented using the components of the example computer system 300 illustrated and described in more detail with reference to FIG. 3. Likewise, embodiments of the system 700 can include different and/or additional components or can be connected in different ways.

In embodiments, the surgical robot 702 includes a controller 704, memory 706, and at least one robotic arm 712 with an end effector 714. The surgical robot 702 can further include a user interface 710 for accepting control inputs from a user, such as a surgeon or other medical professional, and a communications interface 708 for transmitting and receiving data to and from a cloud 720 for the purpose of training an artificial intelligence. The artificial intelligence can operate within the surgical robot 702 or receive remote commands from a remote user, or the artificial intelligence can exist external to the surgical robot 702. The surgical robot 702 can additionally include a plurality of sensors 716 for providing feedback to the user or an artificial intelligence.

A controller 704 is a computing device that includes a processor for performing computations and communicates with a memory 706 for storing data. The controller 704 is in communication with a communications interface 708 and can further be allowed to control the at least one robotic arm 712 and end effector 714 of a surgical robot 702. The controller 704 can be a commercially available central processing unit (CPU) or graphical processing unit (GPU) or can be a proprietary, purpose-built design. Multiple controllers 704 can operate in tandem and can be of different types, such as a CPU and a GPU. A GPU is not restricted to only processing graphics or image data and can be used for other computations.

Memory 706 is the electronic circuitry within a computing device that temporarily stores data for usage by the controller 704. The memory 706 can additionally include persistent data storage for storing data used by the controller 704. The memory 706 can be integrated into a controller 704 or can be a discrete component. The memory 706 can be integrated into a circuit, such as soldered on a component of a single board computer (SBC), or can be a removable component, such as a discrete dynamic random-access memory (DRAM) stick, secure digital (SD) card, flash drive, solid state drive (SSD), magnetic hard disk drive (SSD), etc. In some embodiments, memory 706 can be part of a controller 704. Multiple types of memory 706 can be used by the surgical robot 702.

A communications interface 708 allows the surgical robot 702 to communicate with external devices and can include a wireless antenna and transceiver or a port for receiving a cable to facilitate a wired connection. Examples of a wired connection include ethernet, universal serial bus (USB) or a proprietary connection. A wireless communications interface 708 can include any of Wi-Fi, Bluetooth, near field communications (NFC) or a cellular communications interface such as 3G, 4G, LTE, or 5G. The communications interface 708 can connect a user interface 710 to the surgical robot 702 or can facilitate access to a local network or a cloud 720 network to access a remote server and/or database.

A user interface 710 is a means of interacting with a surgical robot 702 and can include any of a keyboard, computer mouse, trackball, joystick, wireless or wired gamepad, sliders, scroll wheels, touch screen or microphone for receiving voice commands. The user interface 710 can additionally include any method of interaction of a user with a surgical robot 702 not listed. The user interface 710 can accept direct inputs, such as from a joystick controlling the movement of a robotic arm, or indirect inputs (e.g., commands entered on a keyboard or touch screen), such as adjusting the sensitivity of a joystick control or the speed of movement of a robotic arm 712 in response to a joystick. The user interface 710 can also include a screen for presenting information to the user, such as patient status, imaging data, and navigation data, and speakers for providing auditory feedback. The user interface 710 can also utilize haptics to provide feedback to the user. In additional embodiments, the user interface 710 can include an augmented reality (AR) or virtual reality (VR) headset to enable a surgeon to view images from at least one imaging device 718 in real time and can additionally include an overlay, such as an overlay highlighting the blood vessels forming a path along which the catheter must be advanced to access the treatment site, such as a blood clot. The user interface 710 can additionally include voice or eye tracking controls.

A robotic arm 712 is a mechanically actuated arm or lever with at least two degrees of freedom. A robotic arm 712 will typically include at least one of an end effector 714 or an imaging device 718 and can include both an end effector 714 and an imaging device 718. The robotic arm 712 can additionally be capable of changing the end effector 714 to facilitate multiple functions and operation of a variety of tools. The robotic arm 712 can be manually controlled or operated in an autonomous or semi-autonomous mode. A surgical robot 702 can have one robotic arm 712 or multiple robotic arms 712, each of which can be operated independently by one or more users or autonomous systems or by a combination of users and autonomous systems. An end effector 714 is the end of a robotic arm 712 that is conducting work. The end effector 714 is typically a tool or device for interacting with a physical object and can be a surgical tool intended for acting upon or within a patient or can be a gripping device for securing a separate surgical tool to a robotic arm 712.

The end effector 714 can be permanently affixed to the end of a robotic arm 712 or can be detachable, allowing for a system of interchangeable end effectors 714 that can alternatively be selected and swapped by a single robotic arm 712 or multiple robotic arms 712. The end effector 714 can include a catheter or other tool for accessing a treatment site within a patient. Similarly, the end effector 714 can relate to a deployable device, such as a stent, prior to deployment in a patient. The end effector 714 can be constructed of materials that intentionally absorb, reflect, or are transparent to X-rays to facilitate visibility of the end effector 714 when viewed using angiography, fluoroscopy, or other imaging modalities, or, alternatively, to allow the X-rays to pass through to prevent their interference in images. In some embodiments, the end effector 714 can be made to be selectively transparent to X-rays, such as by changing the profile of the end effector 714 or the X-ray absorbing or reflective components to increase or reduce their visibility to an imaging device 718.

A sensor 716 is a measurement tool for monitoring a characteristic or metric associated with a surgical robot 702, an end effector 714, or a patient. A sensor 716 can be discrete or part of an array or assembly, such as integrated into a catheter. One or more of the sensors 716 can include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 716 can be integrated into the operation of the surgical robot 702 or can monitor the status of a patient. The data acquired by the sensors 716 can be used to train a machine learning algorithm used by the surgical robot 702 or to train an artificial intelligence to control the surgical robot 702. The sensors 716 can additionally include an X-ray dosimeter to monitor the intensity of X-rays being emitted toward the patient to prevent excessive doses of radiation. The sensors 716 can be utilized to reduce the intensity of the X-rays or reduce the duration or increase the interval at which the X-rays are emitted toward the patient to control the dose throughout a procedure.

An imaging device 718 refers to any device capable of collecting data that can be used to create an image, or a representation of a physical structure or phenomena. An imaging device 718 can include any device capable of detecting sound or electromagnetic waves and assembling a visual representation of the detected waves. Imaging devices 718 can collect waves from any part of the electromagnetic spectrum or sounds at any range of frequencies, often as a matrix of independently acquired measurements, with each measurement representing a pixel of a two- or three-dimensional image. These measurements can be taken simultaneously or in series via a scanning process or a combination of methods. Some pixels of an image produced by an imaging device 718 can be interpolated from direct measurements representing adjacent pixels in order to increase the resolution of a generated image. Imaging devices 718 can receive or generate imaging data from a plurality of imaging devices 718.

The plurality of imaging devices 718 can include, for example, cameras attached to the robotic arm 712; cameras mounted to the ceiling or other structure above the surgical theater; cameras that can be mounted on a tripod or other independent mounting device; cameras that can be body worn by the surgeon or other surgical staff; cameras that can be incorporated into a wearable device, such as an AR device like Google Glass, Microsoft HoloLens, etc.; cameras that can be integrated into an endoscopic, microscopic, laparoscopic, or any other camera or imaging device 718 (e.g., ultrasound) that can be present in the surgical theater.

The imaging device 718 can include any algorithm or software module capable of determining qualitative or quantitative data from medical images, which can be, for example, a deep learning algorithm that has been trained on a data set of medical images. An imaging device 718 can further refer to a device used to acquire medical images by any means, including magnetic resonance imaging (MRI), computed tomography (CT), X-ray, positron emission tomography (PET), ultrasound, arthrography, angiography, fluoroscopy, myelography, etc. An imaging device 718 can acquire images in real time or be used to create composite images or models in real time. Acquiring images may include selecting one or more imaging modalities based on a region of the anatomy (e.g., a region of interest of the patient). For example, the imaging device may obtain at least one image for each imaging modality of the selected modalities and generate a multi-modality image based on the one or more images.

In some examples, the system 700 may obtain one or more images of an anatomy of the patient using one or more imaging devices, such as imaging device 718, and identify one or more anatomical structures of the anatomy by performing digital image analysis on the one or more images as described herein. The system 700 may generate a mapping of the vasculature in a plurality of dimensions based on the one or more anatomical structures using mapping module 730. In embodiments, system 700 determines, by a machine learning model (e.g., trained by training module 728) using the mapping, an anomalous condition within the vasculature.

In embodiments, system 700 determines, by a rule-based model using the mapping, an anomalous condition within the vasculature. The rule-based model is configured, using data from historical surgical procedures, to identify anomalous conditions associated with vasculatures. The rule-based model is configured using a set of rules that indirectly specifies a mathematical model. The rules can either be translated into a model such as Markov chains or differential equations, or be treated using tools that directly work on the rule-set in place of a translated model. The rule-based model is especially effective in cases where the rule-set is significantly simpler than the model it implies, meaning that the model is a repeated manifestation of a limited number of patterns.

The anomalous condition may be a hemorrhage, a blood clot, internal bleeding, a flow restriction, or an aneurysm. The system 700 can determine an incision site on the anatomy for inserting the surgical instrument (e.g., any of the surgical tools described herein) into the anatomy based on the mapping and the anomalous condition, determine a treatment site based on a location of the anomalous condition, and generate a route for navigating the surgical instrument from the incision site to the treatment site through the vasculature, the route comprising at least a portion of one or more blood vessels. Generating the route for navigating the surgical instrument may include selecting the route from the one or more potential routes based on the one or more metrics.

In embodiments, system 700 generates instructions for surgical robot 702 for inserting a surgical instrument into an anatomy at an incision site. System 700 generates instructions for surgical robot 702 for navigating the surgical instrument from the incision site to the treatment site along the route to treat the anomalous condition.

In embodiments, system 700 inserts, using surgical robot 702, the surgical instrument into the anatomy at the incision site and navigate, by the surgical robot, the surgical instrument from the incision site to the treatment site along the route to treat the anomalous condition. The system 700 may be used to virtually simulate navigation of the surgical instrument through the vasculature to determine one or more metrics for each route of one or more potential routes generated by the machine learning model using the mapping.

A cloud 720 is a distributed network of computers including servers and databases. A cloud 720 can be a private cloud 720, where access is restricted by isolating the network such as preventing external access, or by using encryption to limit access to only authorized users. Alternatively, a cloud 720 can be a public cloud 720, where access is widely available via the internet. A public cloud 720 may not be secured or can include limited security features.

A patient database 722 stores patient data, including electronic medical records, diagnosed conditions, patient-specific baseline values (e.g., heart rate, blood pressure, etc.), and medical imaging data. The patient database 722 can additionally include personal identifiable information, insurance and billing information, personal contact information, and emergency contact information. The patient database 722 can also contain legal documentation, such as consent to perform a procedure. The patient database 722 can further include familial relationships and genetic data to facilitate a comprehensive family history.

In embodiments, system 700 configures a rule-based model to identify an anomalous condition. Data used to configure the rule-based model describes at least one of routes taken by surgical tools 154 through vasculature during historical surgical procedures, or patient outcomes for the historical surgical procedures. In embodiments, system 700 virtually simulates navigation of a surgical instrument through a vasculature to determine one or more metrics for each route of one or more potential routes generated by the rule-based model using the mapping. Generating the route for navigating the surgical instrument comprises selecting the route from the one or more potential routes based on the one or more metrics.

In some aspects of the present invention, a patient database 722 stores medical images that can be used by a training module 728, mapping module 730, and/or navigation module 732. The modules can determine aspects of the patient's anatomy that can affect a surgical procedure and/or the navigation of a catheter or end effector 714 through a patient's body, specifically the patient's vasculature. As referenced herein, a vasculature of a patient may refer to a portion of, multiple portions of, and/or an entire vascular system of a patient. The vascular system may be a system relating to, affecting, or consisting of a vessel or vessels, especially those which carry blood (e.g., blood vessels).

The medical images can additionally include annotations from a practitioner and/or an algorithm indicating tissue types, structures, and/or other anatomical features that can be used by the training module 728, mapping module 730, and/or navigation module 732 to identify conditions such as a clot, hemorrhage, flow restriction, etc. or to modify the procedure.

A procedure database 724 can store data related to surgical or therapeutic procedures including the type of procedure, actions taken during the procedure, what is treated by the procedure, possible contraindications or complications, and resources required, such as personnel, hard goods, and consumables. The procedure database 724 can additionally include the steps of a procedure or instructions for guiding a surgeon or surgical robot 702 through a procedure. A procedure database 724 can additionally include images, including 3D models, that can be used to perform or execute a procedure. The procedure database 724 can be populated by medical professionals or third-party sources and can be used by the training module 728, mapping module 730, and/or navigation module 732.

A base module 726 triggers a training module 728, which queries a procedure database 724 and can additionally query a patient database 722 to retrieve training data. The training data is used to train a machine learning model and the simulations are performed to test the trained model to acquire a confidence in the accuracy of the model. According to some embodiments, the training module may train the machine learning model to identify anomalous conditions such as a hemorrhage, a blood clot, internal bleeding, a flow restriction, or an aneurysm. In some cases, the trained model is trained using one or more images classified based on a location of an anomalous condition of a plurality of subjects. The training sets may also describe at least one of the routes taken by surgical tools through the vasculatures during the historical surgical procedures and patient outcomes for the historical surgical procedures. If the model confidence is high, the trained model will be saved to the procedure database 724, otherwise additional training data will be selected and the process of training and simulating the model will be repeated. The trained model is received by the base module 726, the patient is imaged using at least one imaging device 718, and the mapping module 730 is triggered.

The mapping module 730 receives the image data. Based on the image data, the mapping module identifies anatomical structures, and maps the vasculature. Further, the mapping module identifies an anomalous condition using the image data. The mapping module 730 further identifies one or more incision sites and a treatment site. The mapping module 730 generates multiple routes to the treatment site. A route from the plurality of generated routes is selected and the selected route is saved to the patient database 722. For example, obtaining a route generated using an output of a trained model may include retrieving a route based on a user selection of the route from one or more potential routes generated using the output of the trained model, e.g., a user may select an option on a graphical display (e.g., using a mouse or touchscreen), using a keyboard, using voice control, eye tracking, etc. The selected route is received by the base module 726 and the navigation module 732 is triggered and is sent the selected route.

The navigation module 732 further images the patient, identifies the tool location, and determines whether the tool is on the selected route. If the tool is on the selected route, the navigation module 732 determines whether the tool is at the treatment site. If the tool is on the correct route (e.g., the selected route) but is not yet at the treatment site, the navigation module 732 provides advancement instructions to the surgeon or surgical robot 702 and advances the tool. The navigation module 732 further acquires an image and repeats the process of identifying the tool location and checking whether the tool is on the correct route. If the tool is not on the correct route or the tool is at the treatment site, the base module 726 receives the navigation status. The base module 726 determines whether the tool is at the treatment site and, if so, executes the treatment and ends the procedure. If the tool is not at the treatment site, the navigation module 732 triggers the mapping module 730 to generate new route instructions if necessary. The training module 728 queries the procedure database 724 and can additionally query the patient database 722 for data to train at least one machine learning model. The system 700 may also generate one or more control signals based on the one or more instructions and transmit the one or more control signals to a surgical robot controlling the surgical instrument.

The retrieved data can include image data, which can additionally include annotations from a surgeon, radiologist, other medical professional, or an automated system. Simulations are then performed using test data from the procedure database 724 and/or the patient database 722 to test the confidence of the trained model. If the trained model has a high confidence level, indicated by being above a predetermined threshold value, the model is saved to the procedure database 724, otherwise additional training data is selected and the model is retrained. After the model confidence is sufficiently high, the model is sent to the base module 726.

The mapping module 730 receives image data from the base module 726 and identifies anatomical structures and maps the vasculature. Using the mapped images and a machine learning model trained by the training module 728, the mapping module 730 identifies at least one anomalous condition. An anomalous condition can include a blood clot, hemorrhage, flow restriction, etc. The training module 728 further identifies the treatment site, which is generally the location of a clot, bleed, etc., and generates a plurality of routes through the vasculature to the treatment site. One route is selected from the plurality of routes and the route is saved to the patient database 722 and sent to the base module 726.

According to some embodiments, the mapping module 730 may also generate a virtual anatomy corresponding to the anatomy of the patient. For example, the virtual anatomy may include the mapping of the patient's vasculature and/or one or more identified anatomical structures. For example, the virtual anatomy may include a mapping of one or more identified blood vessels corresponding to one or more blood vessels of the patient.

The navigation module 732 receives the selected route from the base module 726 and acquires live images of the patient from at least one imaging device 718. A machine learning algorithm trained by the training module 728 then identifies the tool location, such as the tip of a catheter, and determines whether the tool is on the selected route. In some examples, determining whether the surgical instrument is on the route includes overlaying one or more images of the patient (e.g., obtained from one or more of imaging devices 718) over a generated virtual anatomy (e.g., generated by mapping module 730) of the patient and comparing the location of the surgical instrument to the route. If the tool is on the selected route, the navigation module 732 determines whether the tool is at the treatment site. If the tool is on the selected route but is not at the treatment site, the navigation module 732 provides advancement instructions to the surgeon or surgical robot 702 and then advances the tool. If the tool is not on the selected route, or has arrived at the treatment site, the navigation module 732 sends the navigation status to the base module 726. The navigation status can indicate that the tool has deviated from the selected route or that the tool has arrived at the treatment site. For example, the advancement instructions may be displayed on one or more graphical displays.

In embodiments, the system of FIG. 7 obtains a route generated using an output of a trained model based on multiple locations of one or more blood vessels of a patient. For example, the trained model can be the ML model 216 illustrated and described in more detail with reference to FIG. 2. One or more images of an anatomy of the patient are captured using one or more imaging devices 718. Using the one or more images, a location of a surgical instrument is determined. The system of FIG. 7 determined that the surgical instrument is on the route a particular distance from a treatment site. For example, the particular distance can be 1 mm, 2 mm, 3 mm, etc. Based on the location of the surgical instrument, one or more instructions are generated for advancing the surgical instrument along the route. The system of FIG. 7 displays, on a graphical display, the one or more instructions for advancing the surgical instrument. For example, the graphical display can be user interface 710. In embodiments, the surgical instrument is at least one of a catheter or an end effector.

In embodiments, the system of FIG. 7 determines a position of a surgical instrument based on one or more images. A planned position of the surgical instrument in a surgical plan is compared to the determined position of the surgical instrument. The system of FIG. 7 determines whether the surgical instrument is at an unacceptable position based on the comparison. In response to determining the surgical instrument is at the unacceptable position, corrective instructions are generated for repositioning the surgical instrument.

FIG. 8 is a chart illustrating a patient database. The patient database 722 includes data about one or more patients and can include electronic medical records. The patient database 722 can include personally identifiable information, such as name, date of birth, address, insurance information, etc. A patient database 722 can additionally include information about a patient's health or medical history, such as diagnosed conditions, allergies, medications, normal baseline vital sign ranges for the patient, etc. Likewise, embodiments of the patient database 722 can include different and/or additional components or can be arranged in different ways.

The patient database 722 can be populated by medical professionals such as a patient's physician, specialists such as surgeons, therapists, or any other medical professionals including nurses, emergency medical technicians, paramedics, etc. The patient database 722 additionally stores images acquired by the base module 726 using at least one imaging device 718 and can additionally store data related to the patient from the mapping module 730 and/or the navigation module 732. The patient database 722 is used by the base module 726, training module 728, mapping module 730, and navigation module 732. The patient database 722 can include, for example, medical images produce by imaging device 718, which can be, for example, X-rays, CT (computed tomography) scan, MRI, ultrasound and nuclear medicine imaging, including positron emission tomography (PET). Medical images can further include still images or videos from a camera either external or internal to the patient, such as an endoscope, laparoscope, etc. Medical image data can include metadata from the images, such as the specific model of equipment used to generate the image, the date and time the image was taken, the geographic location of the image, the anatomical location of the image, the practitioner(s) who performed the imaging, etc. Additionally, the medical image data can include annotations from a practitioner and/or algorithm that can indicate tissue types, structures and/or other anatomical features. The patient database 722 can contain 3D anatomical representations of the user generated by medical images, such as, for example, using the cross-sectional imaging data provided by an MRI device to convert pixels from individual cross-sections into voxels defining a 3D volume by extrapolating the volume between at least two pixels of at least two medical images, wherein the volume can be determined by the distance between cross-sections that the MRI machine generated. The 3D anatomical representation can further be generated by combining cross-sectional images from two or more axial planes of an imaging modality, such as MRI.

FIG. 9 is a chart illustrating a procedure database. The procedure database 724 includes data about one or more surgical procedures. The data can include the steps of the procedure and can also include a plurality of alternative steps or responses to issues or complications. The data can additionally include one or more parameters or conditions by which the procedure can be halted or aborted. The data can additionally include actions taken, measurements taken, such as vital signs, and personnel involved, including the patient, surgeon, and any other personnel and equipment used. Likewise, embodiments of the procedure database 724 can include different and/or additional components or can be arranged in different ways.

The procedure database 724 can be populated by surgeons, nurses, or any other medical professionals or technicians and can include relevant portions of a patient's electronic medical records pertaining to a procedure. The procedure database 724 can additionally include sensor 716 measurements or actions taken by a surgical robot 702 operating in a fully automated capacity, being controlled manually by a surgeon, or operating in a semi-automatic capacity in tandem with a surgeon. In some embodiments, the procedure database 724 can additionally include patient data, such as the data in patient database 722, that can be relevant to one or more procedures. The procedure database 724 can also include procedures that are not relevant to vascular interventions. The procedure database 724 is used by the training module 728, mapping module 730, and navigation module 732. The procedure database 724 can include data related to vascular procedures such as performing a thrombectomy, atherectomy, stent placement, endovascular coiling, clipping (e.g., aneurysm clipping), intravascular medication delivery, angioplasty, etc. In such examples, the procedure data can include instructions for route data including one or more incision sites, one or more treatment sites, and a plurality of routes between one or more incision sites and one or more treatment sites. One or more of the routes can further be selected as preferred routes or, alternatively, be scored and/or ranked to aid selection of a preferred route.

Figure 10:
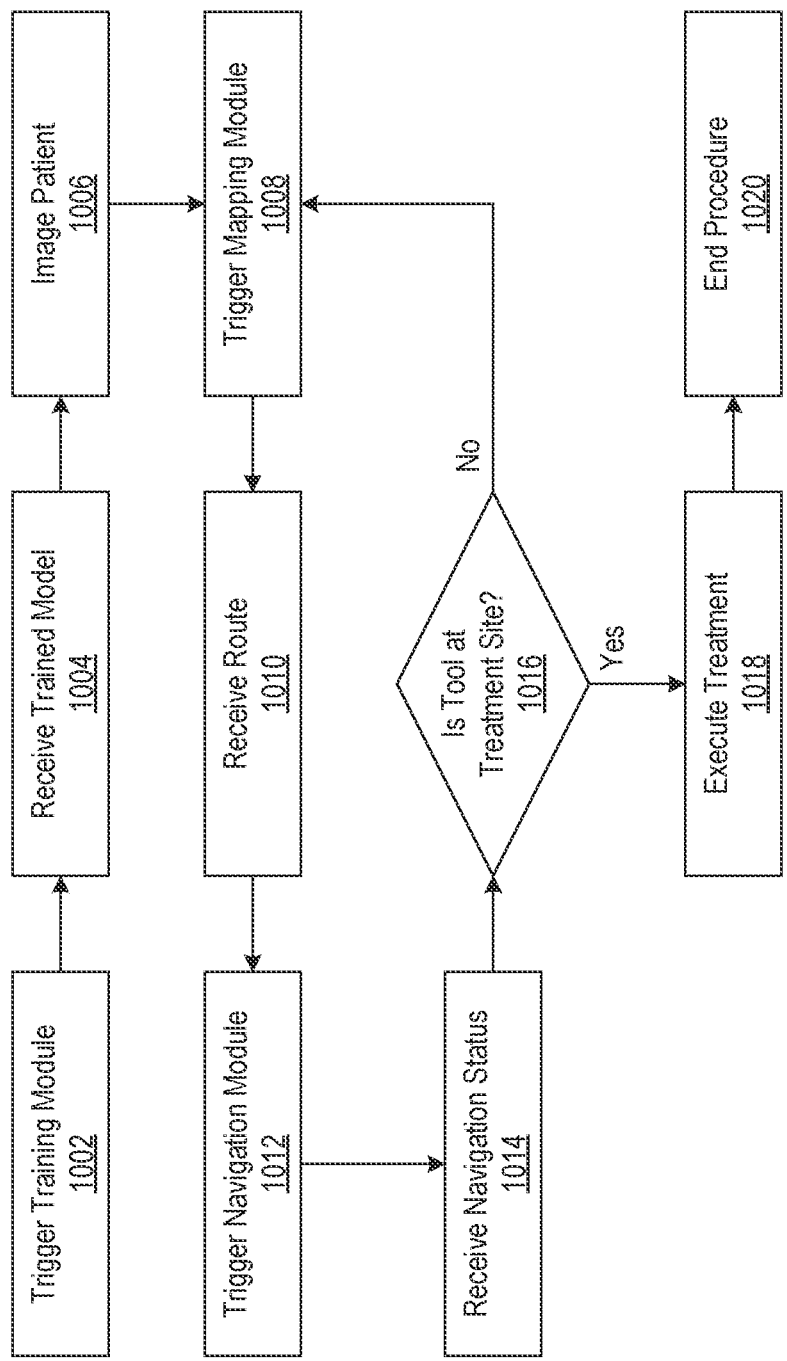
FIG. 10 is a flow diagram illustrating a process performed by a base module, in accordance with one or more embodiments.

FIG. 10 is a flow diagram illustrating a process performed by a base module. In embodiments, the process of FIG. 10 is performed by the base module 726. The base module 726 is illustrated and described in more detail with reference to FIG. 7. In other embodiments, the process of FIG. 10 is performed by a computer system, such as the example computer system 300 illustrated and described in more detail with reference to FIG. 3. Particular entities, for example, the console 108 or the robotic surgical systems 160, 700, perform some or all of the steps of the process in other embodiments. The console 108 and the robotic surgical systems 160, 700 are illustrated and described in more detail with reference to FIGS. 1 and 7. Likewise, embodiments can include different and/or additional steps or perform the steps in different orders.

In step 1002, the base module 726 triggers the training module 728. The training module 728 queries the procedure database 724 for historical data from previously performed procedures. The training module 728 further selects training data from the retrieved data, including data relevant to the route that a tool, an end effector 714, or a catheter took through a patient's vasculature, and outcome data including complications, short-term and long-term condition of the patient, and whether the condition being treated was resolved or not. The training data is used to train a machine learning model and a portion of the training data is further reserved as test data to simulate the accuracy of the trained model. If the accuracy of the trained model is high (indicated by a high confidence interval), the trained model is saved to the procedure database 724. If the accuracy of the trained model is not high (having a confidence interval below a predetermined threshold), the process of selecting training data and training the model is repeated.

In step 1004, the base module 726 receives a trained machine learning model from the training module 728. The trained model can be capable of identifying a medical condition relating to a patient's vasculature, such as the presence and location of one or more clots, bleeding, reduced blood flow, aneurysms, etc. The trained model additionally is capable of mapping a patient's vasculature in two or three dimensions based upon images received from one or more imaging devices 718, and the trained model is further capable of identifying a plurality of routes between possible incision sites and the treatment location. In some embodiments, a single trained model can be capable of all necessary functions. In alternate embodiments, multiple trained models can be utilized, each trained for a specialized function, such as identifying the presence and location of a medical condition, mapping a vasculature, generating routes through the vasculature, identifying the optimal route, etc.

In step 1006, the imaging device 718 images the patient, including the location of a suspected medical condition. The imaging can be performed using at least one of any imaging methods, including both visual light and radiologic modalities; however, in preferred embodiments, at least one imaging modality is a radiologic modality, such as X-ray, CT, MRI, PET, etc. In some embodiments, a single imaging modality can be used, such as MRI. In other embodiments, multiple imaging modalities can be used, such as MRI, CT, and ultrasound. In some embodiments, a single image frame can be used. In other embodiments, multiple image frames can be used. When multiple image frames are used, multiple images can be used to create a higher resolution two-dimensional image. The same method can be applied in slices of varying depths or from varying orientations to create a three-dimensional representation of the print site. In a preferred embodiment, the patient is imaged using X-rays or by using modalities such as angiography and fluoroscopy. In an embodiment, the brain of the patient, John Smith, is imaged using angiography, as he is suspected to be having a stroke. The image data can be further saved to the patient database 722.

In step 1008, the base module 726 triggers the mapping module 730. The mapping module 730 is sent the image data of the patient acquired from at least one imaging device 718 and the one or more trained models trained by the training module 728. The mapping module 730 uses a trained model to identify anatomical structures and map the patient's vasculature. The mapping module 730 further identifies an anomalous condition, such as a clot, reduced blood flow, bleed, aneurism, etc., and further identifies the location of the anomalous condition's cause, such as the location of a clot, source of a bleeding blood vessel, etc. Multiple routes are generated between one or more incision sites and the treatment site, and each route is simulated and scored. One route is selected from the plurality of routes and is saved to the patient database 722.

In step 1010, the base module 726 receives the selected route from the mapping module 730. The selected route can include at least an incision site, a treatment site, and a path through the patient's vasculature from the incision site to the treatment site. The route can include a series of intersections of branching vasculature and instructions about which branch to navigate through. The route can additionally include route parameter data, including the minimum and maximum diameter of the vasculature or a detailed mapping of vascular diameters over the length of the route, predicted elasticity of the blood vessels, etc. In an embodiment, a route from an incision site on the left groin of the patient, John Smith, is received, as well as further directions from the incision site to the treatment site in the brain of the patient where a clot has been identified. A route may also include one or more blood vessels of the vasculature.

In step 1012, the base module 726 triggers the navigation module 732. The navigation module 732 receives the selected route data, including the incision site, treatment site, and instructions for navigating through the patient's vasculature from the incision site to the treatment site, from the base module 726. The navigation module 732 images the patient using at least one imaging device 718, identifies the tool location, and determines whether the tool is on the selected route. If the tool is on the selected route, the navigation module 732 determines whether the tool is at the treatment site. If the tool is not at the treatment site, the navigation module 732 provides advancement instructions to the surgical robot 702 and/or surgeon and advances the tool according to the provided instructions. If the tool is not on the selected route or has arrived at the treatment site, the navigation module 732 returns a navigation status to the base module 726.

In step 1014, the base module 726 receives a navigation status from the navigation module 732. The navigation status includes the current location of the tool being advanced through the patient, which can be an end effector 714 of a surgical robot 702 or a catheter. The navigation status can include notification that the tool has arrived at the treatment site, or, alternatively, that the tool is no longer on the selected route.

In step 1016, the base module 726 determines whether the tool is at the treatment site. The navigation status can provide a binary status indicating whether the tool is or is not at the treatment site. Alternatively, the location of the tool can be compared with the location of the treatment site, and the tool is considered to be at the treatment site if within a predetermined distance, such as 0.5 cm, of the treatment site. If the tool is not at the treatment site, the base module 726 returns to step 1008 and triggers the mapping module 730 to identify a new route or instructions.

In step 1018, the base module 726 executes the treatment according to the procedure. For example, the procedure can be a thrombectomy and the treatment includes the grasping and removal of a clot lodged in the patient's brain. Alternatively, the clot can be mechanically or chemically broken up. Alternative treatments can include the installation of a stent.

In step 1020, the base module 726 ends the procedure, which can include the removal of all tools, end effectors 714, catheters, etc., from the patient and closure of any incision sites. Ending the procedure can additionally include monitoring the patient's condition and treating any complications.

Figure 11:
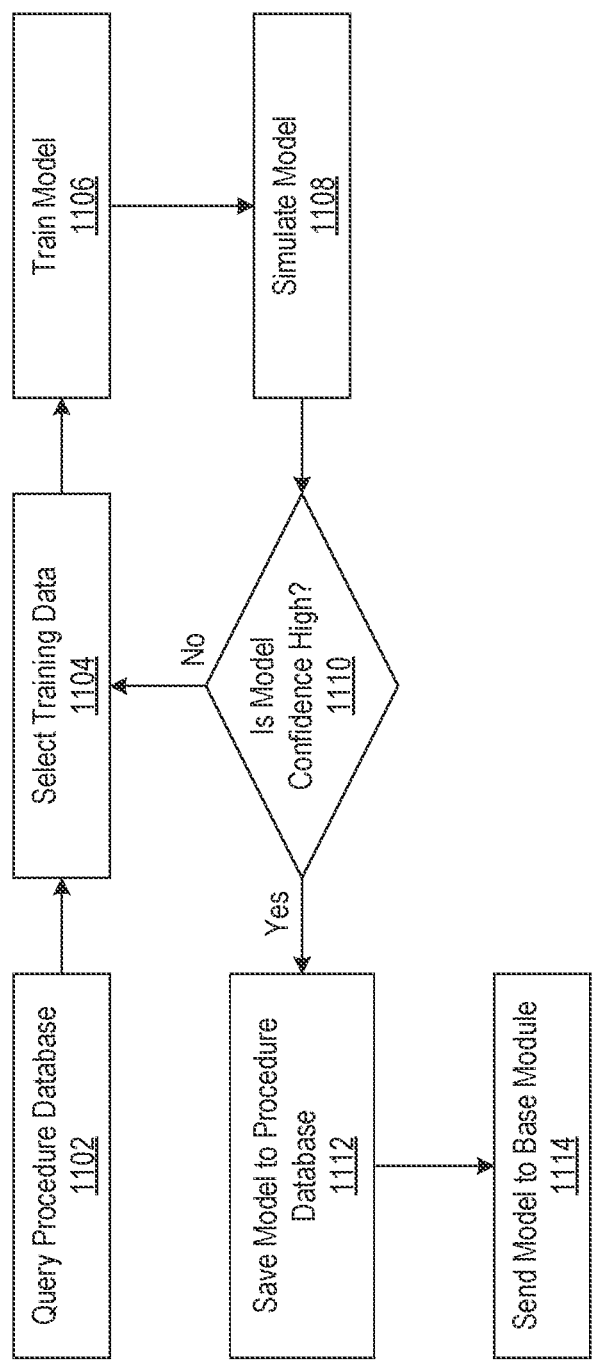
FIG. 11 is a flow diagram illustrating a training module, in accordance with one or more embodiments.

FIG. 11 is a flow diagram illustrating a training module. In embodiments, the process of FIG. 11 is performed by the training module 728. The training module 728 is illustrated and described in more detail with reference to FIG. 7. In other embodiments, the process of FIG. 11 is performed by a computer system, such as the example computer system 300 illustrated and described in more detail with reference to FIG. 3. Particular entities, for example, the console 108 or the robotic surgical systems 160, 700 perform some or all of the steps of the process in other embodiments. The console 108 and the robotic surgical systems 160, 700 are illustrated and described in more detail with reference to FIGS. 1 and 7. Likewise, embodiments can include different and/or additional steps, or perform the steps in different orders.

In step 1102, the training module 728 queries the procedure database 724 for procedure data, including the type of procedure, steps taken during the procedure, and patient outcomes. The data can additionally include images acquired by one or more imaging devices 718 prior to, during, and after the procedure. The patient database 722 can be additionally queried for similar information relating to procedures completed on specific patients. Similarly, data can be retrieved from third-party sources via the cloud 720.

In step 1104, the training module 728 selects training data from the procedure data retrieved from the procedure database 724 and optionally from the patient database 722 and third-party sources via the cloud 720. The training data can vary depending on the type of model being trained. For example, a model can be trained to identify an abnormal medical condition, in which case the training data can include raw image data and additionally classified image data paired with the raw image data, wherein the classified image data indicates that an abnormal medical condition is present and further that the location of the abnormality is identified. A model for mapping a vasculature can similarly receive the same image data, but the classified image data can instead indicate all locations in the images where vasculature is present and can further include depth information to differentiate between different vasculature that can be at varying depths within the patient. Similarly, training data to train a model to navigate a vasculature can include a map of a patient's vasculature, possible incision sites, a treatment site, the preferred routes taken through the patient, and the patient's outcome, i.e., whether the procedure was successful or unsuccessful. The training data can additionally include data from healthy patients in which no abnormal conditions exist.

In step 1106, the training module 728 trains at least one machine learning model. The one or more models are trained to collectively identify the presence and location of an abnormal medical condition, such as a blood clot, bleed, reduction in blood flow, aneurysm, etc., map the patient's vasculature, and generate routes from one or more possible incision sites to the location of the abnormal condition, and further selecting the optimal route from the available routes. The one or more models can be trained via supervised, unsupervised, or a combination of supervised and unsupervised learning methods. Examples of machine learning models include classification, regression, deep learning, convolutional neural networks, etc. The model can be trained to recognize one or more tissue structures, such as the circulatory system and/or the lymphatic system. If multiple models are being trained, they can be trained independently of one another.

In step 1108, the training module 728 simulates the model by using test data to predict the outcome data and further comparing the predictions to the outcome data. An example of a prediction can be to identify the location and type of abnormal medical condition in the provided images. Upon making a prediction, the training module 728 compares the results to the actual outcome. For example, the model is provided an image of a patient's brain acquired using angiography and the model identifies a blood clot in the upper-right quadrant. The training module 728 compares the prediction to a second image where the location of the clot is identified and determines that the model correctly identified the clot in the upper-right quadrant. Alternatively, the model's prediction can have been incorrect if the clot was incorrectly located; if the abnormal condition was not a clot, but instead can have been a condition such as a bleed or an aneurysm; or if no condition was identified when one was, in fact, present. Simulations can include data from healthy patients in which no abnormal condition exists. If multiple models are being trained, each model can be simulated independently or in succession.

In step 1110, the training module 728 determines whether there is a high confidence level in the accuracy of the trained model. The confidence level can be indicated by a statistical confidence interval to determine whether the model is capable of correctly performing its intended function with satisfactory accuracy with a high degree of certainty, whether it be correctly identifying the location and type of abnormal medical condition, correctly mapping a patient's vasculature, or generating routes and selecting the optimal route between an incision site and a treatment site. For example, if the confidence interval is 95.3% and a predetermined threshold is 97.0%, then the confidence interval is not high enough and additional data and/or training is required. If the confidence interval is 98.1%, the confidence interval is above the threshold and is sufficiently high.

In step 1112, the training module 728 saves the trained model to the procedure database 724. In some embodiments, one model can be trained to be capable of performing all necessary functions. In other embodiments, multiple distinct models can be trained each to perform a specific function. Reference to a trained model can refer to either a single, multifunctional model or a collection of single-function trained models.

In step 1114, the training module 728 sends the trained model to the base module 726. In some embodiments, the trained model can include a plurality of trained models such that they collectively perform the necessary functions described herein.

Figure 12:
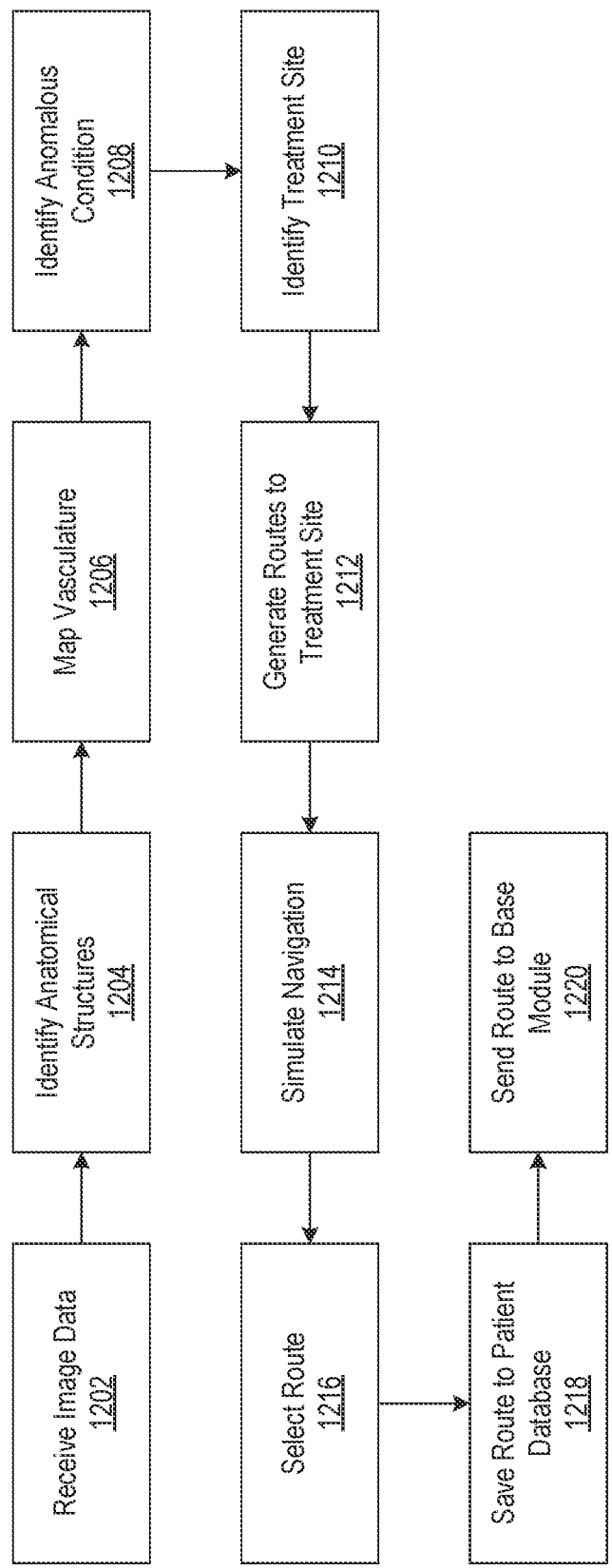
FIG. 12 is a flow diagram illustrating a mapping module, in accordance with one or more embodiments.

FIG. 12 is a flow diagram illustrating a mapping module. In embodiments, the process of FIG. 12 is performed by the mapping module 730. The mapping module 730 is illustrated and described in more detail with reference to FIG. 7. In other embodiments, the process of FIG. 12 is performed by a computer system, such as the example computer system 300 illustrated and described in more detail with reference to FIG. 3. Particular entities, for example, the console 108 or the robotic surgical systems 160, 700 perform some or all of the steps of the process in other embodiments. The console 108 and the robotic surgical systems 160, 700 are illustrated and described in more detail with reference to FIG. 1. Likewise, embodiments can include different and/or additional steps, or perform the steps in different orders.

In step 1202, the mapping module 730 receives the image data from the base module 726. Alternatively, the mapping module 730 receives a reference location or other identifying information to facilitate retrieval of the image data from the patient database 722. In an embodiment, the image data includes a series of images acquired using angiography or fluoroscopy and including the vasculature of the patient, John Smith's, brain. In a further embodiment, a contrast dye is injected into the patient's blood vessels to improve the visibility of the patient's blood vessels.

In step 1204, the mapping module 730 identifies anatomical structures in the image data. The anatomical structures can include bones, organs, etc., that can be used as landmarks for mapping a patient's vasculature and additionally for aligning the mapped vasculature to a real-time image during a procedure such as a thrombectomy. According to some embodiments, the mapping module 730 may also generate a virtual anatomy corresponding to the anatomy of the patient. For example, the virtual anatomy may include the mapping of the patient's vasculature and/or one or more identified anatomical structures.

In step 1206, the mapping module 730 maps the vasculature visible in the image data received from the base module 726. In an embodiment, the vasculature includes the patient's blood vessels visible in the image. In an alternate embodiment, the vasculature includes vessels of the lymphatic system or a combination of vessels of the lymphatic system and blood vessels. The vasculature may not include all vessels that are present, because vessels that located behind a blood clot, or other form of occlusion or reduction in blood flow may not be visible to an imaging device 718, particularly when a dye is required to make the vessels visible. In an embodiment, the vasculature of patient John Smith's brain is mapped. Mapping of the vasculature can utilize edge detection image processing techniques to identify the presence of blood vessels, and images acquired from multiple positions and orientations, to determine the positions of the blood vessels in three-dimensional space. The identified blood vessels can appear as a gradient where lighter intensity can indicate that a vein is deeper, or further from the X-ray emitter.

In step 1208, the mapping module 730 identifies an anomalous condition. An anomalous condition can include any of a blood clot, bleed, aneurism, restriction in blood flow, etc. More than one anomalous condition can be present, and, likewise, all anomalous conditions present and visible via the image data should be identified. In some embodiments, the anomalous conditions identified cannot be restricted to conditions of the vasculature. For example, a condition can include an impingement on one or more blood vessels caused by the swelling of an organ causing a reduction or stoppage in blood flow, such as intercranial swelling resulting from a blunt trauma and skull fracture. In some embodiments, a surgeon, radiologist, or other medical professional can manually identify the anomalous condition type and location. In an embodiment, the anomalous condition is a clot located in the upper-right quadrant of John Smith's brain.

For example, the mapping module 730 analyzes patient data to generate a virtual model of an anomalous condition for virtually simulating, for example, fluid mechanics (e.g., blood flow, blood pressures, etc.), stresses in vasculature walls, or eluting of medicants from implants. In embodiments, the system of FIG. 7 virtually simulates the narrowing of vessels, atherosclerosis (e.g., long-term plaque buildup based on family history), etc. The mapping module 730 can analyze lipoprotein-related markers, family history data of atherosclerosis, lipid levels, and other patient data to perform long-term simulations of vascular function, outcome for treated anomalous condition, etc. Vascular parameters are used by the virtual simulations to determine predicted outcomes. For example, the virtual simulations use a minimum and/or a maximum diameter of the vasculature at a particular location, a predicted amount of elasticity of blood vessels, or risk scores for blood vessels that are narrowed or stiffened by plaque buildup to determine predicted outcomes. In embodiments, the virtual simulations use parameters related to stresses in vasculature walls, eluting of medicants from implants, or narrowing of vessels to determine predicted outcomes. In embodiments, the virtual simulations use atherosclerosis-related parameters, lipoprotein-related markers, or family history data of atherosclerosis to determine predicted outcomes. In embodiments, the virtual simulations use lipid levels to determine predicted outcomes.

The mapping module 730 can predict the likelihood of one or more adverse events associated with candidate or planned treatments. Example vascular adverse events can include, for example, vessel trauma, atherosclerosis, vessel rupture, thrombosis, or the like. The mapping module 730 can use one or more machine learning models (e.g., models trained using training sets from historical surgical procedures with adverse events) to identify potential adverse events and modify treatment to reduce or eliminate the risk of the potential adverse event.

In step 1210, the mapping module 730 identifies a treatment site. A treatment site is the location within the vasculature closest to the anomalous condition and what is generally determined to be the cause of the anomalous condition. For example, the treatment site is the location of a clot, source of a bleeding vessel, the base of an aneurysm, location of restricted blood flow, etc. In some cases, the treatment site cannot be the cause of the anomalous condition, but instead can be where an intervention can occur. For example, in the case of a patient suffering from intercranial swelling, a blood vessel can be collapsed due to the pressure. The location of the collapse can be the treatment site, where a stent can be placed to keep the blood vessel open. In an embodiment, the treatment site is within 0.5 cm of a blood clot in John Smith's brain.

In step 1212, the mapping module 730 generates multiple routes from one or more potential incision sites to the treatment site. Each route includes an incision site and a path from the incision site to the treatment site. In some embodiments, each route can additionally include route parameters such as the minimum and maximum diameter of the vasculature, length of the route, number of branches encountered, etc. In an embodiment, a route is generated from an incision site on the left groin to the treatment site. In an alternate embodiment, a route is generated from an incision site on the right groin to the treatment site. In an embodiment, routes are generated by tracing from the treatment site toward one or more potential incision sites against the flow of blood through the patient's arteries. In an alternate embodiment, a list of available incision sites is retrieved from the procedure database 724 or selected by a surgeon, and an incision site is selected by tracing routes from each of the available incision sites toward the treatment site. A route must successfully form a path from the incision site to the treatment site. The routes can additionally include instructions for a surgeon or surgical robot 702, such as directions about when to advance a tool and which vessel to proceed through when approaching a branch in the vasculature. The instructions additionally include checkpoints, such that when a tool is advanced to a checkpoint, the next step is prompted and delivered to the surgical robot 702 or surgeon, providing instructions to the surgical robot 702 or surgeon to navigate to the next checkpoint.

In step 1214, the mapping module 730 simulates the navigation of a tool, end effector 714, catheter, etc. from an incision site through the route to the treatment site. The simulations can additionally predict the elasticity of the vasculature and generate risk scores for the route based upon the route parameters and patient data that can be available via the patient database 722. For example, a patient with a history of atherosclerosis can have a lower predicted elasticity of the vasculature and consequently a higher risk score. The simulations can use the route parameters to assign an overall score considering the risk score and determining the route with the highest likelihood of success while minimizing the risk of complications.

In step 1216, the mapping module 730 selects a route from the plurality of routes based on the results of the simulation. The simulations can provide a score for each route and the route with the highest score can be selected. Alternatively, the route can be selected based upon which one has the lowest risk of complications. Alternatively, a route can be selected based on the fewest number of branches. The route can be selected after considering the preferences of the surgeon. In some embodiments, some or all of the routes can be provided to a surgeon who can select their preferred route. In an embodiment, a route is selected from an incision site on the left groin to the treatment site. In some embodiments, multiple routes can be selected, such as if multiple tools must be deployed or there are multiple treatment sites.

In step 1218, the mapping module 730 saves the route to the patient database 722. The route can include the simulation results and detailed instructions for navigating from the selected incision site to the treatment site. In some embodiments, all of the generated routes and the simulation results can be saved to the patient database 722.

In step 1220, the mapping module 730 sends the selected route to the base module 726. The selected route includes detailed instructions for navigating from the incision site to the treatment site based upon the simulation data. The route data can additionally include route parameters that can be used to determine the maximum size of tool, end effector 714, catheter, etc., which can be navigated to the treatment site.

Figure 13:
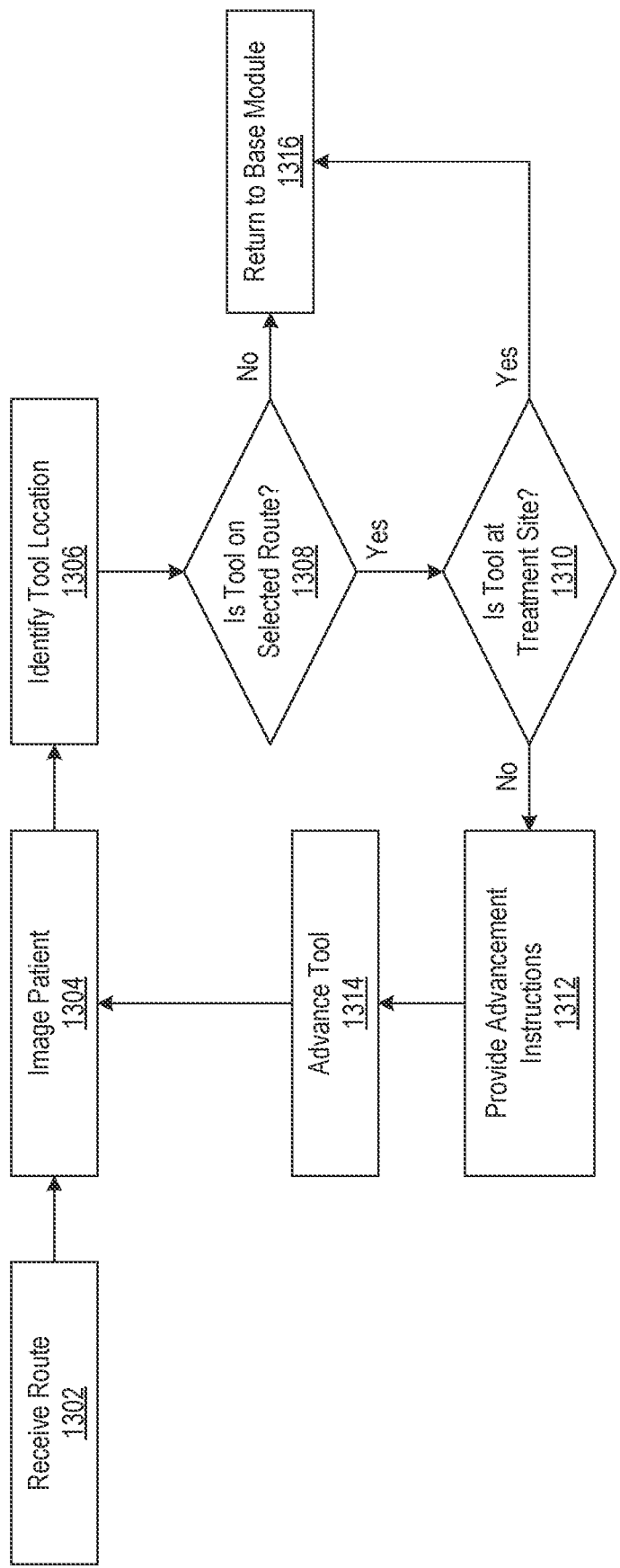
FIG. 13 is a flow diagram illustrating a navigation module, in accordance with one or more embodiments.

FIG. 13 is a flow diagram illustrating a navigation module. In embodiments, the process of FIG. 13 is performed by the navigation module 732. The navigation module 732 is illustrated and described in more detail with reference to FIG. 7. In other embodiments, the process of FIG. 13 is performed by a computer system, such as the example computer system 300 illustrated and described in more detail with reference to FIG. 3. Particular entities, for example, the console 108 or the robotic surgical systems 160, 700 perform some or all of the steps of the process in other embodiments. The console 108 and the robotic surgical systems 160, 700 are illustrated and described in more detail with reference to FIGS. 1 and 7. Likewise, embodiments can include different and/or additional steps, or perform the steps in different orders.

In step 1302, the navigation module 732 receives route data from the base module 726. The route data can include a treatment site, an incision site, and a route through a patient's vasculature from the incision site to the treatment site. The route data can additionally include route parameters, such as the maximum and minimum diameters of the blood vessels in the route, or can include the diameter of the blood vessels along the entire route. Similarly, route parameters can include a predicted amount of elasticity of the blood vessels or risk scores for part or the entirety of the route, such as blood vessels that are narrowed or stiffened by plaque buildup. In an embodiment, route data is received for a route from an incision site on the left groin to the upper-right quadrant of patient John Smith's brain.

In step 1304, the navigation module 732 images the patient, including the treatment site. The imaging can be performed using at least one of any imaging method using X-rays, ideally including angiography or fluoroscopy. In alternate embodiments, other imaging modalities can be used, such as MRI. The imaging can be conducted continuously in real time or can be sampled at a regular interval. The imaging interval can vary based on data, including sensor 716 data from a dosimeter to ensure the total amount of X-rays administered to the patient does not exceed a threshold value. In an embodiment, the brain of John Smith is imaged using angiography during a thrombectomy. The image data can be further saved to the patient database 722. The process of imaging the patient can additionally include registration to the previously mapped vasculature performed by the mapping module 730. Contrast dye can be injected to improve the visibility of the vessels.

In step 1306, the navigation module 732 identifies the location of the tool being inserted into the patient's vasculature. The tool location can be any point between the incision site and the treatment site. The tool can be within the selected route or can deviate from the selected route via intentional or unintentional action. The tool can be an end effector 714 of a surgical robot 702 or a catheter. The tool can be engineered to be visible under X-rays, such as using materials and geometry that either absorb or reflect X-rays. The tool can be selectively transparent to X-rays such that only the head of the tool is visible under X-rays and the remaining portion of the inserted tool is transparent so that the tool does not interfere with images of the vessels beneath the tool. In an embodiment, the tool is a catheter, and the head of the catheter is located in the lower-right quadrant of the brain at a branching point.

In step 1308, the navigation module 732 determines whether the tool is on the selected route by overlaying the previously mapped vasculature to the real-time images and comparing the location of the tool to the route. Additionally or alternatively, the virtual anatomy may be overlaid. If the tool is in the vasculature in the real-time images corresponding to the previously acquired, mapped, and planned route images, then the tool is on the selected route. If the tool is in a vessel that does not correspond to the selected route, then the tool is not on the selected route. In an embodiment, the tool is on the correct route.

In step 1310, the navigation module 732 determines whether the tool is at the treatment site. The tool is at the treatment site if the tool is within a predetermined threshold of the treatment site. The treatment site is located in the real-time images that corresponds to the previously acquired images which was used by the mapping module 730 to identify the type and location of the condition, the treatment site, and the selected route. In an embodiment, the tool is 0.3 cm from the clot at the treatment site, which is within the threshold of 0.5 cm from the treatment site and therefore indicates that the tool is at the treatment site. In an alternate embodiment, the tool is 2.6 cm from the treatment site, which is greater than the threshold of 0.5 cm from the treatment site and therefore indicates that the tool is not at the treatment site.

In step 1312, the navigation module 732 provides advancement instructions to the surgical robot 702 and/or the surgeon as generated by the mapping module 730. The advancement instructions can be specific directions, such as to advance a tool or catheter a specific distance through the patient's vasculature. The directions can additionally indicate which of a plurality of branches that can be ahead of the tool should be navigated through. The directions can additionally include context warnings, such as when the tool or catheter is approaching blood vessels that can be compromised by conditions such as atherosclerosis, or are in close proximity to sensitive tissues. The advancement instructions can be provided audibly, via a user interface 710 such as a terminal screen, or via an AR or VR headset. Alternatively, the advancement instructions can include digital instructions or control signals that direct a surgical robot 702 to advance an end effector 714 within the patient in a comparable manner to those instructions provided to a surgeon, but executable by a surgical robot 702. The advancement instructions can include a hybrid of manual and digital inputs such that a surgeon can be advised of the correct route and can provide manual input and direction to the surgical robot 702. In alternate embodiments, the advancement instructions can include direction to retract the tool in the event the tool was advanced too far or down the wrong branch. In an embodiment, the advancement instructions include the direction to advance a catheter 1.2 cm.

In step 1314, the navigation module 732 advances the tool through the patient according to the advancement instructions. Advancing the tool can be performed manually by a surgeon, semi-autonomously by a surgeon providing manual instructions to a surgical robot 702, or fully autonomously by a surgical robot 702. A procedure performed fully autonomously by a surgical robot 702 can be supervised by a surgeon who can intervene at any point they deem necessary. In an embodiment, the surgical robot 702 advances the catheter 1.2 cm inside the vasculature. After advancing the tool, the navigation module 732 returns to step 704 and images the patient.

In step 1316, the navigation module 732 returns to the base module 726 and provides a navigation status. The navigation status indicates whether the tool has arrived at the treatment site, and, if not, can include additional information about the tool location and the procedure status, which can be sent to the mapping module 730 to generate new or updated route instructions. In an embodiment, the navigation status includes a notification that the tool has arrived at the treatment site. In an alternate embodiment, the navigation status includes a notification that the tool is not on the selected route and has instead navigated into an incorrect branch.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A computer-implemented digital image analysis method for navigating a surgical instrument through a vasculature of a patient using a surgical robot, comprising:
   obtaining one or more images of an anatomy of the patient using one or more imaging devices;
   identifying one or more anatomical structures of the anatomy by performing digital image analysis on the one or more images, the one or more anatomical structures comprising at least one or more blood vessels of the patient;
   generating a mapping of the vasculature in a plurality of dimensions based on the one or more anatomical structures;
   determining, by a machine learning model using the mapping, an anomalous condition within the vasculature, the machine learning model trained, using training sets from historical surgical procedures;
   determining a treatment site based on a location of the anomalous condition;
   determining at least one incision site for inserting the surgical instrument into the vasculature based on the treatment site:
   generating a plurality of intravascular routes for navigating the surgical instrument from the at least one incision site to the treatment site through the vasculature;
   virtually simulating navigation of the surgical instrument through the vasculature by simulating the surgical instrument positioned within and moving along the at least one or more blood vessels of the vasculature to determine one or more metrics for each route of the plurality of intravascular routes based on an interoperative goal and/or a post-operative goal;
   selecting a route from the plurality of intravascular routes for navigating the surgical instrument based on the one or more metrics;
   after selecting the intravascular route, inserting, by the surgical robot, the surgical instrument into the anatomy at the at least one incision site; and
   navigating, by the surgical robot, the surgical instrument from the at least one incision site to the treatment site along the intravascular route to treat the anomalous condition.

2. The method of claim 1, wherein the anomalous condition comprises at least one of a hemorrhage, a blood clot, internal bleeding, a flow restriction, or an aneurysm.

3. The method of claim 1, comprising training the machine learning model to identify the anomalous condition, wherein the training sets describe at least one of:
   intravascular routes taken by surgical tools through vasculatures during the historical surgical procedures; and
   patient outcomes for the historical surgical procedures.

4. The method of claim 1, comprising:
   selecting one or more imaging modalities based on a region of the anatomy, wherein obtaining the one or more images of the anatomy comprises obtaining at least one image for each imaging modality of the one or more imaging modalities; and
   generating a multi-modality image based on the one or more images.

5. The computer-implemented digital image analysis method of claim 1, wherein the one or more images is a first one or more images, the method comprising:
   obtaining a second one or more images of the anatomy using the one or more imaging devices;
   identifying, using the second one or more images, a location of the surgical instrument;
   overlaying the second one or more images on the mapping; and
   generating, based on the location of the surgical instrument, an instruction for advancing, by the surgical robot, the surgical instrument toward the treatment site.

6. The computer-implemented digital image analysis method of claim 5, wherein the instruction is a first instruction, the method comprising:
    determining that the surgical instrument is located off the intravascular route; and
    generating, based on the location of the surgical instrument, a second instruction for advancing, by the surgical robot, the surgical instrument toward the intravascular route.

7. A surgical robot for navigating a surgical instrument through a vasculature of a patient, comprising:
    a non-transitory computer-readable storage medium storing computer instructions, which when executed by one or more computer processors cause the surgical robot to:
        obtain one or more images of an anatomy of the patient using one or more imaging devices;
        identify one or more anatomical structures of the anatomy by performing digital image analysis on the one or more images, the one or more anatomical structures comprising at least one or more blood vessels of the patient;
        generate a mapping of the vasculature in a plurality of dimensions based on the one or more anatomical structures;
        determine, by a machine learning model using the mapping, an anomalous condition within the vasculature, the machine learning model trained, using training sets from historical surgical procedures;
        determine a treatment site based on a location of the anomalous condition;
        determine at least one incision site for inserting the surgical instrument into the vasculature based on the treatment site;
        generate a plurality of intravascular routes for navigating the surgical instrument from the at least one incision site to the treatment site through the vasculature;
        virtually simulate navigation of the surgical instrument through the vasculature by simulating the surgical instrument positioned within and moving along the at least one or more blood vessels of the vasculature to determine one or more metrics for each route of the plurality of intravascular routes based on an interoperative goal and/or a post-operative goal;
        select a route from the plurality of intravascular routes for navigating the surgical instrument based on the one or more metrics;
        after selecting the intravascular route, insert, by the surgical robot, the surgical instrument into the anatomy at the at least one incision site; and
        navigate, by the surgical robot, the surgical instrument from the at least one incision site to the treatment site along the intravascular route to treat the anomalous condition.

8. The surgical robot of claim 7, wherein the anomalous condition comprises at least one of a hemorrhage, a blood clot, internal bleeding, a flow restriction, or an aneurysm.

9. The surgical robot of claim 7, wherein the computer instructions cause the surgical robot to perform operations comprising:
    training the machine learning model to identify the anomalous condition, wherein the training sets describe at least one of:
        intravascular routes taken by surgical tools through vasculatures during the historical surgical procedures; and
        patient outcomes for the historical surgical procedures.

10. The surgical robot of claim 7, wherein the computer instructions cause the surgical robot to perform operations comprising:
    selecting one or more imaging modalities based on a region of the anatomy, wherein obtaining the one or more images of the anatomy comprises obtaining at least one image for each imaging modality of the one or more imaging modalities; and
    generating a multi-modality image based on the one or more images.

11. The surgical robot of claim 7, wherein the one or more images is a first one or more images, and wherein the computer instructions cause the surgical robot to perform operations comprising:
    obtaining a second one or more images of the anatomy using the one or more imaging devices;
    identifying, using the second one or more images, a location of the surgical instrument;
    overlaying the second one or more images on the mapping; and
    generating, based on the location of the surgical instrument, an instruction for advancing, by the surgical robot, the surgical instrument toward the treatment site.

12. The surgical robot of claim 11, wherein the instruction is a first instruction, and wherein the computer instructions cause the surgical robot to perform operations comprising:
    determining that the surgical instrument is located off the intravascular route; and
    generating, based on the location of the surgical instrument, a second instruction for advancing, by the surgical robot, the surgical instrument toward the intravascular route.

13. A system for navigating a surgical instrument through a vasculature of a patient using a surgical robot, comprising:
    one or more computer processors; and
    a non-transitory computer-readable storage medium storing computer instructions, which when executed by the one or more computer processors cause the system to:
        obtain one or more images of an anatomy of the patient using one or more imaging devices;
        identify one or more anatomical structures of the anatomy by performing digital image analysis on the one or more images, the one or more anatomical structures comprising at least one or more blood vessels of the patient;
        generate a mapping of the vasculature in a plurality of dimensions based on the one or more anatomical structures;
        determine, by a machine learning model using the mapping, an anomalous condition within the vasculature, the machine learning model trained, using training sets from historical surgical procedures;
        determine a treatment site based on a location of the anomalous condition;
        determining at least one incision site for inserting the surgical instrument into the vasculature based on the treatment site:
        generate a plurality of intravascular routes for navigating the surgical instrument from the at least one incision site to the treatment site through the vasculature;

virtually simulate navigation of the surgical instrument through the vasculature by simulating the surgical instrument positioned within and moving along the at least one or more blood vessels of the vasculature to determine one or more metrics for each route of the plurality of intravascular routes based on an interoperative goal and/or a post-operative goal;

select a route from the plurality of intravascular routes for navigating the surgical instrument based on the one or more metrics;

after selecting the intravascular route, insert, by the surgical robot, the surgical instrument into the anatomy at the at least one incision site; and navigate, by the surgical robot, the surgical instrument from the at least one incision site to the treatment site along the intravascular route to treat the anomalous condition.

14. The system of claim 13, wherein the anomalous condition comprises at least one of a hemorrhage, a blood clot, internal bleeding, a flow restriction, or an aneurysm.

15. The system of claim 13, wherein the computer instructions cause the one or more computer processors to perform operations further comprising:

training the machine learning model to identify the anomalous condition, wherein the training sets describe at least one of:

intravascular routes taken by surgical tools through vasculatures during the historical surgical procedures; and patient outcomes for the historical surgical procedures.

16. The system of claim 13, wherein the computer instructions cause the one or more computer processors to perform operations further comprising:

selecting one or more imaging modalities based on a region of the anatomy, wherein obtaining the one or more images of the anatomy comprises obtaining at least one image for each imaging modality of the one or more imaging modalities; and generating a multi-modality image based on the one or more images.

17. The system of claim 16, wherein the computer instructions cause the one or more computer processors to perform operations further comprising:

obtain a second set of images of an anatomy of the patient captured using one or more imaging devices;

identify, using the second set of images, a location of the surgical instrument;

overlay one or more images of the second set of images over a virtual anatomy;

determine that the surgical instrument is on the intravascular route and is not in the treatment site; and generate, based on the location of the surgical instrument, one or more instructions for advancing the surgical instrument along the intravascular route.

* * * * *